(12) United States Patent
Bopardikar et al.

(10) Patent No.: US 11,072,776 B2
(45) Date of Patent: Jul. 27, 2021

(54) FOETAL POLYMIX OF MESENCHYMAL STEM CELLS UNDER HYPOXIC CONDITIONS FOR THE TREATMENT OF CLINICAL DISORDERS AND DISEASES

(71) Applicant: Reelabs Private Limited, a Company Incorporated Under Provisions of The Companies Act 1956, Mumbai (IN)

(72) Inventors: Abhijit Bopardikar, Mumbai (IN); Rohit Kulkarni, Mumbai (IN); Sunil Pophale, Mumbai (IN)

(73) Assignee: Reelabs Private Limited, a Company Incorporated Under Provisions of The Companies Act 1956, Mumbai (IN)

( * ) Notice: Subject to any disclaimer, the term of this patent is extended or adjusted under 35 U.S.C. 154(b) by 390 days.

(21) Appl. No.: 15/295,939

(22) Filed: Oct. 17, 2016

(65) Prior Publication Data
US 2017/0029770 A1 Feb. 2, 2017

Related U.S. Application Data

(63) Continuation-in-part of application No. PCT/IN2015/000205, filed on May 8, 2015.

(30) Foreign Application Priority Data

May 9, 2014 (IN) ............... IN1603/MUM/2014

(51) Int. Cl.
| | | |
|---|---|---|
| C12N 5/073 | (2010.01) |
| A61K 8/98 | (2006.01) |
| A61K 35/50 | (2015.01) |
| A61K 35/51 | (2015.01) |
| C12N 5/0775 | (2010.01) |
| A61K 35/28 | (2015.01) |
| A61K 9/00 | (2006.01) |

(52) U.S. Cl.
CPC ............ *C12N 5/0605* (2013.01); *A61K 8/982* (2013.01); *A61K 9/0019* (2013.01); *A61K 35/28* (2013.01); *A61K 35/50* (2013.01); *A61K 35/51* (2013.01); *C12N 5/0668* (2013.01); *A61K 2800/91* (2013.01); *C12N 2500/02* (2013.01); *C12N 2500/32* (2013.01); *C12N 2502/1388* (2013.01); *C12N 2509/00* (2013.01)

(58) Field of Classification Search
None
See application file for complete search history.

(56) References Cited

U.S. PATENT DOCUMENTS

| | | | | |
|---|---|---|---|---|
| 5,906,915 A | * | 5/1999 | Payrat ............... | A01N 1/0226 424/93.73 |
| 2005/0244963 A1 | | 11/2005 | Teplyashin | |
| 2007/0015278 A1 | * | 1/2007 | Li ................. | C12N 5/0605 435/366 |
| 2010/0124569 A1 | | 5/2010 | Abbot et al. | |
| 2012/0141975 A1 | * | 6/2012 | Sato ................. | A61M 1/02 435/2 |
| 2012/0225096 A1 | * | 9/2012 | Paludan ............. | A61K 35/50 424/278.1 |

FOREIGN PATENT DOCUMENTS

| | | |
|---|---|---|
| EP | 2368974 A1 | 9/2011 |
| EP | 2594636 A2 | 5/2013 |
| WO | 1994016099 A1 | 7/1994 |
| WO | 2003042405 A2 | 5/2003 |
| WO | 2005001076 A2 | 1/2005 |
| WO | 2006019357 A1 | 2/2006 |
| WO | 2008143578 A1 | 11/2008 |
| WO | 2008146991 A1 | 12/2008 |
| WO | 2008146992 A1 | 12/2008 |
| WO | 2009052132 A1 | 4/2009 |
| WO | 2011101834 A1 | 8/2011 |
| WO | 2012131618 A1 | 10/2012 |
| WO | 2013082417 A1 | 6/2013 |
| WO | 2013172793 A1 | 11/2013 |
| WO | WO 2014/035215 * | 3/2014 |

OTHER PUBLICATIONS

Hass et al., "Different populations and sources of human mesenchymal stem cells (MSC): A comparison of adult and neonatal tissue-derived MSC", Cell Communication and Signaling, 2011, 8:12, pp. 1-14 (Year: 2011).*
Castrechini et al., "Mesenchymal stem cells in human placental chorionic villi reside in a vascular Niche", Placenta 2010, 31(3), pp. 203-212. (Year: 2010).*
Cotyledon defnition, Medical Dictionary, 2009, https://medical-dictionary.the freedictionary.com/cotyledon, pp. 1-3. (Year: 2009).*
Vellasamy et al, "Isolation and characterisation of mesenchymal stem cells derived from human placenta tissue", World Journal of Stem Cells, 2012, 4(6), pp. 53-61. (Year: 2012).*
Boyette et al, "Human Bone Marrow-Derived Mesenchymal Stem Cells Display Enhanced Clonogenicity but Impaired Differentiation With Hypoxic Preconditioning", Stem Cells Translational Medicine, 2014, vol. 3, pp. 241-254. (Year: 2014).*
Dos Santos, F., et al., "Ex Vivo Expansion of Human Mesenchymal Stem Cells: A More Effective Cell Proliferation Kinetics and Metabolism Under Hypoxia," Journal of Cellular Physiology, 223, 2010, pp. 27-35.
Abdollahi, H., et al., "The Role of Hypoxia in Stem Cell Differentiation and Therapeutics," J. Surg. Res., Jan. 2011, 165(1), 9 pages.

(Continued)

*Primary Examiner* — Laura Schuberg
(74) *Attorney, Agent, or Firm* — Rahman LLC

(57) ABSTRACT

A method for isolation, enrichment and co-culture of foetal polymix involving two or more components of mesenchymal stem cells derived from, but not limited to, placenta, amnion, amniotic fluid, chorion and umbilical cord and/or other products of conception under hypoxic or otherwise and/or normoxic/general conditions for treatment of a plurality of disorders ranging from congenital to degenerative to developmental to malignant disorders and diseases prior to therapeutic administration.

5 Claims, 11 Drawing Sheets

(56) References Cited

OTHER PUBLICATIONS

Haque, N., et al., "Hypoxic Culture Conditions as a Solution for Mesenchymal Stem Cell Based Regenerative Therapy," The Scientific World Journal, vol. 2013, Jul. 3, 2013, pp. 1-13.

Maruyama, N., et al., "Hypoxia enhances the induction of human amniotic mesenchymal side population cells into vascular endothelial lineage," International Journal of Molecular Medicine, 32: 2013, pp. 315-322.

* cited by examiner

FOETAL POLYMIX OF MESENCHYMAL STEM CELLS UNDER HYPOXIC CONDITIONS FOR THE TREATMENT OF CLINICAL DISORDERS AND DISEASES

CROSS-REFERENCE TO RELATED APPLICATIONS

This application is a Continuation-in-part of International Application No. PCT/IN2015/000205 with an international filing date of May 8, 2015, which claims priority to Indian patent application no. 1603/MUM/2014 filed May 9, 2014 which is herein incorporated by reference in its entirety.

BACKGROUND

Technical Field

The embodiments herein generally relate to stem cell therapy, and more particularly to a method and a composition for treating diseases or disorders in a subject using a mixture of co-cultured mesenchymal stem cells, and methods for isolating and enriching mesenchymal stem cells from extra embryonic perinatal sources under hypoxic or normoxic conditions prior to therapeutic administration.

Description of the Related Art

Stem cells are undifferentiated cells, which have the potential of differentiating into a various cell types. Stem cells are distinguished from other cell types by two important characteristics. First, they are unspecialized cells capable of renewing themselves through cell division, sometimes after long periods of inactivity. Further, under certain physiologic or experimental conditions, they can be induced to become tissue-specific or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Mesenchymal stem cells (MSCs) are multi-potent stromal cells that can differentiate into a variety of cell types, such as osteoblasts, chondrocytes, myocytes, adipocytes, etc. Mesenchymal stem cells may be isolated from various tissues such as the bone marrow, umbilical cord blood, adipose tissue, etc. Although bone marrow mesenchymal stromal cells (BM-MSCs) are the most studied and well-documented, BM-MSCs have limitations in terms of cell numbers and they require expansion in-vitro, thus running the risk of loss of stemness properties, induction of artifactual chromosomal changes, and contamination. Adipose tissue has recently emerged as an alternative source of MSCs. Despite its plentiful nature, an invasive procedure is still required to collect the tissue.

Also, mesenchymal stem cells derived from bone marrow and adipose cells are adult. Hence, they have a determined cell type and typically cannot be changed into tissues that differ from the ones that they came from. There are numerous studies involving mesenchymal stem cells derived from a specific source (e.g., a specific tissue type). Despite encouraging results from numerous preclinical studies, ongoing clinical trials of stem cell therapy have so far demonstrated moderate and inconsistent benefits or results. Accordingly, there remains a need for a mixture of co-cultured mesenchymal stem cells that have immune-privileged characteristics, that have broader multi-potent plasticity and that proliferate faster than adult MSCs.

The various Mesenchymal Stem Cell Markers of individual sources are as follows:

| Umbilical cord | Amnion | Chorion |
| --- | --- | --- |
| MSCs grow as adherent cells with mesenchymal morphology and in Negative express CD14-, CD34-, CD31, CD45- Positive express CD73, CD90, CD105, CD29, CD44 OCT4, SOX2, NANOG, TERT, SSEA4 Mesenchymal lineage primarily Under specific conditions endodermal lineage, including hepatocyte-like cells UCMSCs in rescuing injured liver functions and reducing fibrosis in vivo chondrogenic capacity could be useful for future cell therapy in articular diseases. neural regeneration upregulate the | fibroblast-like mesenchymal cells and rare macrophages. CD73, CD90, CD105, CD29, CD44 (SSEA)-4, (TRA)1-60, TRA1-81, (OCT)-4, SSEA-3, epithelial cuboid cells and the columnar cells. human amniotic epithelial cells (EA) express stem cell markers have important immunological capacities and can differentiate into all three embryonic layers. Placental stem cells do show similar plasticity and the self-regeneration capacity of embryonic stem cells, they are superior to adult type stem cells. | fibroblast-like mesenchymal cells freshly isolated cells from the placental chorionic villi CD73, CD90, CD105, CD29, CD44 (SSEA)-4, (TRA)1-60, TRA1-81, (OCT)-4, suitability in cellular therapeutics is better illustrated by their fibroblastic morphology, plastic adherence, surface antigenic expression as well as multi-differentiation capacity |

| Umbilical cord | Amnion | Chorion |
|---|---|---|
| production of hyaluronic acid and GAGs, as well as the expression of key genes as SOX9, secrete large amount of growth factors such as EGF, TGF, IGF-1. WJ-MSCs produce large amounts of tolerogenic IL-10 | | |

Mesenchymal Stromal Cell Markers in Polymix

The following markers expressed in Amnion, placenta chorion and umbilical Cord stem cells would be present in the co-culture:

Positive markers for Mesenchymal Stromal Cells: CD90, CD105, CD73, CD29, CD106, CD13, CD146, CD44, CD49e, CD54, CD117, CD166, CD27, and STRO-1.

Negative markers for Mesenchymal Stromal Cells (MSCs):—CD34, CD45, CD14, CD79a, HLA-DR AND CD11b. However recent discovery of numerous embryonic-like stem cells markers like c-KIT, OCT-4, SOX-2, SSEA4, TRA-1-60, TRA-1-81, NANOG etc. in these foetal stem cells further optimizes the pedigree of these sources and hence their co-culture. Hematopoietic markers like CD34+, CD45 are also noted in placenta.

By preparing a suitable concoction (Poly mix) of 1-2 OR 1-3 FSCs in different proportion to come out with single effective stem cell therapy covering broad categories of disorders, a trivial step like hypoxic pre-conditioning to stem cells shall enhance their properties significantly.

The current stem cell therapy protocols do not involve exposure to hypoxia prior to stem cell injection. Hence it is thought worthwhile to replicate body's natural micro environmental hypoxic niche by exposing this stem cell concoction to hypoxia prior to therapeutic administration. This will not only increase stem cell viability, proliferation but also enhance potency of stem cell as a drug significantly. The enhancement of stem cell potency is a need in the industry to increase success rate of stem cell therapy.

SUMMARY

In view of foregoing, the embodiments herein relates to role of hypoxia in a polymix combination of foetal stem cells. An embodiment herein provides a method for isolation, enrichment, and co-culture of a foetal polymix. The method includes providing two or more components of mesenchymal stem cells derived from any of a placenta, amniotic membrane, chorion, amniotic fluid, and umbilical cord in a medium under any of a hypoxic and a normoxic condition. The mesenchymal stem cells are provided as an injectable composition.

The mesenchymal stem cells may include at least two different types of stem cells including any of chorionic villi stem cells, amniotic progenitor cells, avascular amnion stem cells, vascular amnion stem cells, vascular chorion stem cells, and umbilical cord stem cells. The composition may be adapted to be differentiated into progenitor and precursor cells for treating disorders and diseases. The disorders and diseases may comprise any of diabetes mellitus, chronic kidney disease, liver cirrhosis, spinal cord injury, cardiac failure, retinitis pigmentosa, autism, muscular dystrophies, non-union fractures, hair loss, knee osteoarthritis, Parkinson's disease, avascular necrosis, Alzheimer's disease, cerebral palsy, multiple sclerosis, anti-aging, and stroke.

The composition may be administered using any of an intravenous route, an intrathecal route, an intra-articular route, an intramuscular route, a derma roller, a mesogun, a local route, a periorbital route, an intravitreal route, and a retrobular route. The composition may be stored in a plasmolyte solution and a phosphate buffer.

In another aspect, an injectable composition derived from a process for isolation, enrichment, and co-culture of foetal polymix is provided. The composition includes two or more components of mesenchymal stem cells derived from any of a placenta, amniotic membrane, chorion, amniotic fluid, and umbilical cord in a medium under any of a hypoxic and a normoxic condition. The mesenchymal stem cells may include at least two different types of stem cells including any of chorionic villi stem cells, amniotic progenitor cells, avascular amnion stem cells, vascular amnion stem cells, vascular chorion stem cells, and umbilical cord stem cells.

In yet another aspect, a method for isolating mesenchymal stem cells from a placental amniotic membrane is provided. An amniotic membrane is collected from placenta. An amniotic tissue is obtained from the amniotic membrane. The amniotic tissue is subjected to enzymatic digestion in a container with a trypsin solution. A first supernatant is collected from the container. Fetal bovine serum containing Dulbecco's Modified Eagle's Medium (DMEM) and collagenase are added to the container. The container is incubated. A second supernatant is collected from the container. A mixture of the first supernatant and the second supernatant is filtered. A filtrate from the mixture is centrifuged to obtain a pellet.

The pellet may be re-suspended in phosphate buffer solution (PBS) to obtain a re-suspended pellet layer. The re-suspended pellet layer may be added on top of a ficoll density gradient medium to obtain a second mixture. The second mixture may be centrifuged to obtain cells from a middle band. The cells may be washed with PBS to obtain mesenchymal stem cells. The mesenchymal stem cells may be re-suspended in Dulbecco's Modified Eagle's Medium (DMEM) for culturing. Isolated mesenchymal stem cells may be seeded. The seeded isolated mesenchymal stem cells may be incubated until the seeded isolated mesenchymal stem cells reach approximately 70-80% confluence.

In yet another aspect, a method for isolating mesenchymal stem cells is provided. An amniotic membrane is separated from a subjacent chorion. Fragments of the amniotic membrane are transferred to Dulbecco's Modified Eagle's Medium (DMEM) supplemented with fetal bovine serum, glutamine, at least one antibiotic, and non-essential amino acids Amniotic membrane fragments are selected from the DMEM at a level of a reflected portion to obtain selected amniotic membrane fragments. The selected amniotic membrane fragments are fragmented into pieces. The pieces are washed in a phosphate buffer solution. The pieces are subjected to a first enzymatic digestion with a trypsin solution to remove epithelial amniotic cells. The pieces are subjected a second enzymatic digestion with another trypsin solution and collagenase. The pieces that are subjected to the first enzymatic digestion and the enzymatic digestion to fetal bovine serum to obtain a cell suspension. The cell suspension is filtered. A filtrate from the cell suspension is centrifuged to obtain a pellet including mesenchymal stem cells.

The mesenchymal stem cells may be re-suspended in Dulbecco's Modified Eagle's Medium (DMEM) for culturing. Isolated mesenchymal stem cells may be seeded from DMEM. The seeded isolated mesenchymal stem cells may be maintained until the seeded isolated mesenchymal stem cells reach 70-80% confluence.

In yet another aspect, a method for isolating mesenchymal stem cells is provided. An amniotic membrane is collected by removing the amniotic membrane from a chorion. The amniotic membrane is treated with trypsin-ethylenediaminetetraacetic acid (EDTA). The amniotic membrane is washed in saline after being treated with the trypsin-EDTA to obtain a washed amniotic membrane. The washed amniotic membrane is chopped to obtain a chopped amniotic membrane. The chopped amniotic membrane is digested to obtain a digested amniotic membrane. A phosphate buffer solution (PBS) is added to the digested amniotic membrane to obtain a mixture. The mixture is centrifuged to obtain a pellet including cells.

The cells may be re-suspended in a basal culture medium (BCM) and a low glucose Dulbecco's Modified Eagle's Medium (LG-DMEM). Mesenchymal stem cells may be re-suspended from the BCM and the LG-DMEM in DMEM for culturing. Isolated mesenchymal cells may be isolated. The seeded isolated mesenchymal stem cells may be incubated until the seeded isolated mesenchymal stem cells reach 70-80% confluence.

In yet another aspect, a method for isolating mesenchymal stem cells from amniotic fluid is provided. The amniotic fluid is collected. The amniotic fluid is centrifuged to obtain a first pellet. The first pellet is re-suspended in a phosphate buffer solution (PBS). The PBS including the first pellet is centrifuged to obtain a second pellet. The second pellet is re-suspended in another PBS. The PBS including the second pellet is centrifuged to obtain mesenchymal stem cells. Isolated mesenchymal stem cells may be seeded from Dulbecco's Modified Eagle's Medium (DMEM). The seeded isolated mesenchymal stem cells may be incubated until the seeded isolated mesenchymal stem cells reach 70-80% confluence.

In yet another aspect, a method for isolating mesenchymal stem cells from a placenta is provided. A chorionic trophoblast is collected from the placenta. The chorionic trophoblast is washed with a sterile phosphate buffer solution (PBS). An area is selected from the chorionic trophoblast that contains chorionic villi. The areas are minced into a plurality of pieces. Collagenase and dispase are added to a container containing minced chorionic trophoblast for digestion. The container is incubated. Fetal bovine serum is added to the container to inhibit activity of collagenase and dispase. A mixture is filtered in the container. A filtrate is centrifuged from the mixture to obtain a pellet.

The pellet may be re-suspended in another PBS to obtain a re-suspended pellet layer. The re-suspended pellet layer may be added on top of a ficoll density gradient medium to obtain a mixture. The mixture may be centrifuged to obtain cells from a middle band. The cells may be washed with PBS to obtain mesenchymal stem cells. The mesenchymal stem cells may be re-suspended in Dulbecco's Modified Eagle's Medium (DMEM) for culturing. Isolated mesenchymal stem cells may be seeded from DMEM. The seeded isolated mesenchymal stem cells may be incubated until the seeded isolated mesenchymal stem cells reach 70-80% confluence.

In yet another aspect, a method for isolating mesenchymal stem cells from a placenta is provided. A fetal decidua's placental tissue is collected from placenta. The fetal decidua's placental tissue is washed with a phosphate buffer solution (PBS). The fetal decidua's placental tissue is digested with collagenase. Cells are separated by centrifuging a mixture of the fetal decidua's placental tissue and collagenase over a Ficoll-Hypaque separation medium to obtain separated cells.

The separated cells may be re-suspended for culture in L-Dulbecco's Modified Eagle's Medium (LDMEM) supplemented with fetal bovine serum, basic fibroblast growth factor, L-glutamine, and at least one antibiotic. Cells may be seeded from the LDMEM in a culture flask. Non-adherent cells may be removed from the culture flask. Cells may be harvested from the culture flask by adding trypsin and ethylenediaminetetraacetic acid (EDTA). The cells may be passaged.

In yet another aspect, a method for isolating mesenchymal stem cells from a placenta is provided. A chorion is collected from the placenta. The chorion is minced to obtain a minced chorion. The minced chorion is centrifuged to obtain a first pellet. The first pellet is haemolysed with a red blood cell lysis buffer. A mixture including the first pellet and the red blood cell lysis buffer are centrifuged to obtain a second pellet. The second pellet is incubated with a trypsin-ethylenediaminetetraacetic acid (EDTA) solution to obtain a trypsin-EDTA solution treated pellet.

The trypsin-EDTA solution treated pellet may be re-suspended in a minimum essential medium (MEM) or a fetal bovine serum to obtain a re-suspended mixture. The re-suspended mixture may be centrifuged to obtain a third pellet. The third pellet including mesenchymal stem cells may be cultured in a minimum essential medium (MEM) supplemented with fetal calf serum, L-ascorbate-2-phosphate, L-Glutamine, an antibiotic, fungizone, and tylosin.

In yet another aspect, a method for isolating mesenchymal stem cells from an umbilical cord is provided. Blood vessels are incised from the umbilical cord. A first container containing the umbilical cord is incubated with collagenase and dispase. Fetal bovine serum (FBS) containing Dulbecco's Modified Eagle's Medium (DMEM) is added to the first container to inhibit an activity of the collagenase and the dispase. The umbilical cord is crushed in the first container to release cells into a first solution in the first container. The umbilical cord is placed in a second container. The umbilical cord is incubated with trypsin. Fetal bovine serum (FBS) containing Dulbecco's Modified Eagle's Medium (DMEM) is added to the second container to stop activity of trypsin. The umbilical cord is crushed in the second container to release cells into a second solution in the second container. A mixture of the first solution and the second solution is filtered.

A filtrate may be centrifuged from to obtain a pellet including mesenchymal stem cells. The mesenchymal stem cells may be re-suspended in Dulbecco's Modified Eagle's Medium (DMEM) for culturing. Isolated mesenchymal stem cells may be seeded from DMEM. The seeded isolated mesenchymal stem cells may be incubated until the seeded isolated mesenchymal stem cells reach 70-80% confluence.

In yet another aspect, a method for isolating mesenchymal stem cells from an umbilical cord is provided. A processed umbilical cord is subjected to an enzymatic digestion with collagenase and hyaluronidase. A mixture containing the processed umbilical cord, collagenase, and hyaluronidase are incubated with gentle agitation. Trypsin is added to the mixture. The mixture is incubated to obtain a digested suspension. The digested suspension is diluted with phosphate buffer solution (PBS) to obtain a diluted suspension. The diluted suspension is filtered to obtain a single cell suspension.

The single cell suspension may be centrifuged to obtain a pellet. The pellet may be re-suspended in a medium including albumin, hydroxyethyl starch (HES), and citrate-phosphate-dextrose-adenine anticoagulant. Cells containing mesenchymal stem cells may be isolated from the medium. Isolated mesenchymal stem cells from Dulbecco's Modified Eagle's Medium (DMEM) may be seeded. The seeded isolated mesenchymal stem cells may be incubated until the seeded isolated mesenchymal stem cells reach 70-80% confluence.

In yet another aspect, a foetal polymix composition derived into any of progenitor and precursor cells is provided. In yet another aspect, a polymix composition including two or more stem cells selected from any of embryonic and adult sources is provided.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1:
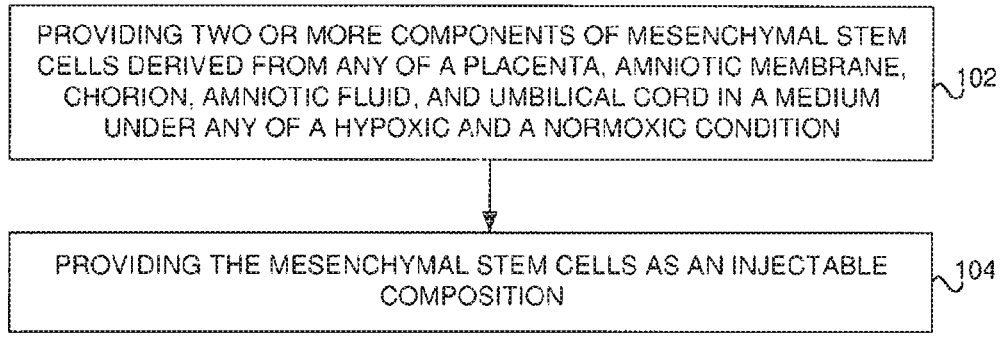
FIG. 1 is a flow diagram illustrating a method for isolating, enriching, and co-culturing of a foetal polymix according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Moreover, the various numeric values and/or ranges described below are given as approximates, and the embodiments herein should not be interpreted to be constrained by the specific values given, unless otherwise indicated. Accordingly, the examples should not be construed as limiting the scope of the embodiments herein.

Referring to the drawings, and more particularly to FIGS. 1 through 11, there are shown embodiments herein. The embodiments herein provide a composition and a method for treating various diseases and disorders in subjects using a mixture of co-cultured mesenchymal stem cells (MSCs) derived from multiple sources, and methods for isolating and enriching such mesenchymal stem cells. The mesenchymal stem cells are derived from two or more sources selected from (i) a placenta, (ii) an amniotic membrane, (iii) a chorion, (iv) an amniotic fluid, and (v) an umbilical cord. The mesenchymal stem cells derived from these sources have immune-privileged characteristics, broader multi-potent plasticity, and they proliferate faster than adult mesenchymal stem cells. The mesenchymal stem cells from the above sources are typically available after a child's birth, without any ethical problems, or any invasive action.

In one embodiment, the mesenchymal stem cells discussed throughout various embodiments herein are derived in-vitro from extra-embryonic perinatal placenta, foetal membrane (including amnion membrane and chorion membrane), umbilical cord, and amniotic fluid. The mesenchymal stem cells from each of the above sources have their own molecular signatures, thus making them suitable for treating particular disease conditions.

The mesenchymal stem cells are isolated and enriched from two or more sources selected from (i) a placenta, (ii) an amniotic membrane, (iii) a chorion, (iv) an amniotic fluid, and (v) an umbilical cord. The mesenchymal stem cells thus isolated and enriched are co-cultured in a culture medium under a hypoxic condition. The term 'co-culture' used herein throughout various embodiments refers to growing more than one distinct cell type in a combined culture medium.

In one embodiment, the mesenchymal stem cells thus isolated and enriched are co-cultured in a Dulbecco's Modified Eagle's Medium (DMEM). The DMEM may be supplemented with fetal bovine serum (FBS), an amino acid (e.g., L-glutamine), and an antibiotic solution. In one embodiment, a flask containing the culture medium that includes mesenchymal stem cells from two or more above sources is incubated in a carbon dioxide ($CO_2$) incubator at 37° C. under hypoxic conditions including approximately 1-3% of oxygen concentration, 5% of carbon dioxide concentration, and 93% of nitrogen concentration.

In one embodiment, a fresh media is added to the culture medium every 24 hours, and the culture medium is changed twice in a week until adherent cells reach 70-80% confluence. A trypsin solution is added to the culture medium to harvest dissociated mesenchymal stem cells. The dissociated mesenchymal stem cells thus harvested include a mixture of co-cultured mesenchymal stem cells. Thus, the term "a mixture of co-cultured mesenchymal stem cells" discussed throughout various embodiments herein refers to mesenchymal stem cells derived from various sources that are grown together in a culture medium under hypoxic conditions.

In one embodiment, the mixture of co-cultured mesenchymal stem cells includes mesenchymal stem cells derived from two or more sources selected from (i) a placenta, (ii) an amniotic membrane, (iii) a chorion, (iv) an amniotic fluid, and (v) an umbilical cord at substantially equal proportions. For example, the mixture of co-cultured mesenchymal stem cells includes 33% amniotic MSCs of the total cell population, 33% chorionic MSCs of the total cell population, and 34% umbilical cord MSCs of the total cell population. In another embodiment, the mixture of co-cultured mesenchymal stem cells includes mesenchymal stem cells derived from two or more sources selected from (i) placenta, (ii) amniotic membrane, (iii) chorion, (iv) amniotic fluid, and (v) umbilical cord at any proportions.

In one embodiment, a composition or a medicament including the mixture of co-cultured mesenchymal stem cells which are obtained by co-culturing mesenchymal stem cells derived from at least two of a group including of (i) placenta, (ii) amniotic membrane, (iii) chorion, (iv) amniotic fluid, and (v) umbilical cord in a medium under a hypoxic condition with a 1 to 3% of oxygen concentration is used for treating various diseases or disorders in subjects. The medicament or the composition is stored in a plasmolyte solution and a phosphate buffer. The medicament or the composition is administered into subjects via route selected from the group including of (i) an intravenous route, (ii) an intrathecal route, (iii) an intra-articular route, (iv) an intramuscular route, (v) a derma roller, (vi) a mesogun, (vii) a local route, (viii) a periorbital route, (ix) an intravitreal route, and (x) a retrobular route.

In one embodiment, a mixture of co-cultured MSCs includes mesenchymal stem cells of different types is used in the treatment of diseases in animals and humans, both male and female mostly caused by degeneration, deficiency or defects of functional cells includes (i) chorionic villi stem cells, (ii) amniotic progenitor cells, (iii) avascular amnion stem cells, (iv) vascular amnion stem cells, (v) vascular chorion stem cells and (vi) umbilical cord stem cells. The medicament or the composition including foetal polymix of co-cultured mesenchymal stem cells under a hypoxic condition produces significantly better results when used in the treatment of animals or human subjects suffering from such diseases or disorders, when compared to the results obtained on treatment with any single type of mesenchymal stem cells.

A composition or a medicament including the mixture of co-cultured mesenchymal stem cells is useful in treating diseases or disorders, including but not limited to, (a) diabetes mellitus, (b) cardiac failure and cardiomyopathies, (c) cerebral palsy, (d) autism, (e) non-union fractures, (f) knee osteoarthritis, (g) avascular necrosis, (h) muscular dystrophies, (i) multiple sclerosis, (j) retinitis pigmentosa, (k) macular degeneration, (l) stroke, (m) Alzheimer's disease, (n) spinal cord injury, (o) Parkinson's disease, (p) liver cirrhosis, (q) chronic kidney disease, (r) hair-loss, (s) anti-aging, and/or (t) senescence.

Different methods for isolating and enriching mesenchymal stem cells from each of the sources selected from (i) amniotic membrane, (ii) chorion, (iii) amniotic fluid, and (iv) umbilical cord are discussed below. It is to be understood by a person having ordinary skill in the art, isolation and enriching of mesenchymal stem cells are not restricted only to the methods discussed below, and the embodiments herein can include other methods and techniques.

Mesenchymal stem cells can be isolated and enriched from placental amniotic membrane in a plurality of ways. A first method for isolating and enriching mesenchymal stem cells from placental amniotic membrane is discussed below.

The surface of the placenta is rinsed with a sterile phosphate buffered saline (PBS) to remove as much blood as possible. The upper amnion layer is pulled with the help of pointed forceps in a container. The amniotic membrane is washed thoroughly with a sterile PBS until it is nearly free of blood. The amniotic membrane, which is washed with the sterile PBS, is placed in a petri plate, and minced. In one embodiment, a part of the amniotic membrane, which is contaminated with red blood cells (RBC) is not selected and minced. The minced amniotic membrane is placed into a sterile container, and is incubated in 0.25% trypsin solution for 30 mm at 37° C. The container is not be disturbed while removing the container from an incubator. Supernatant from the container is removed and collected in a 50 mL centrifuge tube, and is labeled as solution A.

10% fetal bovine serum (FBS) containing Dulbecco's Modified Eagle's Medium (DMEM) is added to the container to stop trypsin activity. Collagenase Type IV is further added to the container depending on the amount of tissue in the container. The container is mixed thoroughly, and is incubated for 1 hour at 37° C. The container is not disturbed while removing the container from an incubator. Supernatant from the container is removed, and is collected in a 50 mL centrifuge tube, and is labeled as solution B. Both solutions A and Solution B are mixed together, and are filtered through a 100 micron cells strainer. Filtrates from the 100 micron cells strainer are centrifuged using a centrifuge apparatus at 1,500 revolutions per minute (rpm) for 10 minutes. A centrifuged solution containing (a) supernatant is discarded, and (b) a pellet is re-suspended with a sterile PBS.

The re-suspended pellet layer is placed on top of a ficoll density gradient medium (e.g., a density of 1.077 g/mL). A gradient is established by centrifuging at 1,500 rpm for 15 minutes. After centrifugation, cells are collected from a middle band of a centrifuged solution. A collected monolayer including cells is washed with PBS twice to obtain mesenchymal stem cells. The mesenchymal stem cells are re-suspended in DMEM for culturing, and are isolated from a culture. The isolated mesenchymal stem cells are seeded at a density of $10^6$ cells per mL of DMEM supplemented with 10% FBS, 1% antibiotic solution and 2 mM L-Glutamine into a culture flask, and are kept in a 5% $CO_2$ incubator. After 24 hours, non-adherent cells are removed from the culture flask, and a fresh media is added to the culture flask. The culture medium is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per $cm^2$ for further culturing.

A second method for isolating and enriching mesenchymal stem cells from placental amniotic membrane is discussed below.

An amniotic membrane is mechanically separated from a subjacent chorion by detachment. Fragments of the amniotic membrane are transferred to petri plates with a DMEM medium supplemented with 10% fetal bovine serum, 2 mML-glutamine, 100 U/mL penicillin, 100 pz/mL streptomycin, and 1% non-essential amino acids. Isolation is carried out from the amnion at a level of reflected portions of the membranes in order to minimize presence of maternal cells. The amniotic membrane is mechanically fragmented, and the resulting fragments are washed with PBS several times, and are submitted to an enzymatic digestion treatment in two stages.

In stage 1, 0.25% trypsin is added to fragments of the amniotic membrane in a container, and the container is incubated at 37° C. for 5 minutes in order to remove epithelial amniotic cells. In stage 2, the container is further treated with 0.25% trypsin and 0.1% collagenase IV for 5 minutes at 37° C., and is followed by inactivation of trypsin activity with fetal bovine serum. A cell suspension from the above processes is filtered through 100 micron cells strainer. Filtrates from the 100 micron cells strainer are centrifuged at 350 g for 5 minutes. A centrifuged solution containing (a) supernatant is discarded, and (b) a pellet containing mesenchymal stem cells is re-suspended in DMEM for culturing, and cells are isolated from a culture.

The isolated mesenchymal stem cells are seeded at a density of $10^6$ cells per mL of DMEM supplemented with 10% FBS, 1% antibiotic solution and 2 mM L-Glutamine into a culture flask, and kept in a 5% $CO_2$ incubator. After 24 hours, non-adherent cells are removed from the culture flask, and fresh media is added to the culture flask. The media is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per $cm^2$ for further culturing.

A third method for isolating and enriching mesenchymal stem cells from placental amniotic membrane is discussed below.

An amniotic membrane is peeled off from a chorion mechanically to separate the amniotic membrane from a whole placenta. The collected amniotic membrane is rinsed with normal saline (0.9%) several times under sterile conditions. The amniotic membrane includes an epithelial monolayer and avascular stroma. The collected amniotic membrane is enzymatically and mechanically treated in two steps. In step 1, the collected amniotic membrane is treated with 0.25% trypsin-EDTA at 37° C. for 30 minutes to avoid contamination of epithelial cells. After trypsin-EDTA treatment, the collected amniotic membrane is washed with normal saline three to four times. In step 2, the washed amniotic membrane is chopped with a surgical blade to isolate pure mesenchymal cells from amniotic membrane without epithelial cells. Chopped amniotic membrane is digested in Collagenase type 1 (2 mg/mL) at 37° C. for approximately three to four hours. After enzyme digestion, the digested amniotic membrane is washed in PBS by centrifugation at 350 g for 5 min.

From a centrifuged solution, a pellet containing cells is obtained, and the cells are re-suspended in a basal culture medium and a low glucose Dulbecco's Modified Eagle's Medium. From the culture medium, mesenchymal stem cells are isolated. The isolated mesenchymal stem cells are seeded at a density of $10^6$ cells per mL of DMEM supplemented with 10% FBS, 1% antibiotic solution and 2 mM L-Glutamine into a culture flask, and are kept in a 5% $CO_2$ incubator. After 24 hours, non-adherent cells are removed from the culture flask, and fresh media is added to the culture flask. The media is changed twice weekly. Once adherent cells reach the 70-80% confluence, the adherent cells are dissociated from the culture media with 0.25% trypsin. In a culture flask, 5,000-10,000 cells are seeded per $cm^2$ of the flask for further culturing.

A fourth method for isolating and enriching mesenchymal stem cells from placental amniotic membrane is discussed below.

An amniotic membrane is separated from chorion through blunt dissection. The collected amniotic membrane is rinsed with phosphate buffer saline several times under sterile conditions. The amniotic membrane is minced, placed in a sterile container, and subjected to 15-minute digestion with 0.25% trypsin-EDTA solution. Supernatant is discarded from the container. The container containing the tissue undergoes a second digestion with 0.25% trypsin-EDTA solution, 10 Mill DNAseI and 0.1% collagenase IV solution in DMEM. Fragments from the second digestion are pipetted vigorously up and down for 5 minutes by avoiding foam. Larger pieces of tissue are allowed to settle under gravity for 5 minutes at 37° C. Supernatant from the container is transferred to a fresh tube, and the supernatant is neutralized with Fetal Bovine Serum (FBS) and then centrifuged at 1,500 rpm for 10 minutes.

Each pellet from a centrifuged solution is re-suspended in 5 mL of culture medium. In one embodiment, the culture medium contains DMEM, 20% FBS, penicillin 100 U/mL and streptomycin 100 lig/mL. Cells are seeded in 25 $cm^2$ flasks, and the hMSC cultures are grown at 37° C. in a 5% $CO_2$. Non-adherent cells are removed from the flasks after 1 week. The medium (with 10% of FBS) is subsequently changed every four days.

In one embodiment, mesenchymal stem cells are isolated and enriched from amniotic fluid by a method as discussed below.

An amniotic fluid is aspirated with 10 cc syringes. The amniotic fluid is collected in 15 mL sterile tubes. The amniotic fluid in 15 mL sterile tubes is centrifuged at 1,500 rpm for 10 minutes. A centrifuged solution containing a pellet is re-suspended in PBS. The pellet and PBS are mixed together, and centrifuged at 1,500 rpm for 10 minutes. A centrifuged solution containing a pellet is again re-suspended in PBS. The pellet and PBS are mixed together, and the mixture is again centrifuged at 1,500 rpm for 10 minutes. Supernatant is discarded, and cells are re-suspended in DMEM for culturing. Cells are isolated from DMEM.

The isolated cells are seeded at a density of $10^6$ cells per mL of DMEM supplemented with 10% FBS, 1% antibiotic solution and 2 mM L-Glutamine into the culture flask and kept in a 5% $CO_2$ incubator. After 24 hours, non-adherent cells are removed from the culture flask, and a fresh media is added. The media is changed twice weekly. Once adherent cells reach the 70-80% confluence, the adherent cells are dissociated from the culture media with 0.25% trypsin. In a culture flask, 5,000-10,000 cells are seeded per cm² of the flask for further culturing.

Mesenchymal stem cells are isolated and enriched from placental chorion in a plurality of ways. A first method for isolating and enriching mesenchymal stem cells from placental chorion is discussed below.

Placenta is washed thoroughly with PBS. After washing the placenta, the amniotic membrane is removed. 200 grams of chorionic trophoblast are collected from the placenta. The chorionic trophoblast is washed thoroughly with a sterile PBS until it is nearly free of blood. Areas rich in chorionic villi are selected and are minced between scalpel blades into small pieces. The minced chorionic trophoblast is transferred to a sterile container. 5 mL of 0.1% Collagenase type IV, and dispase are added into the sterile container in the ratio of 7:1 for digesting the minced chorionic trophoblast. The sterile container is incubated in a 37° C. incubator for 1 hour. After incubation, activity of collagenase type IV and dispase is inactivated by adding 10% FBS containing DMEM to the sterile container. Cells that are released from the sterile container are pooled, and are filtered through 100 micron cell strainer.

Filtrates from the 100 micron cells strainer are centrifuged using a centrifuge apparatus at 1,500 rpm for 10 minutes. A centrifuged solution containing (a) supernatant is discarded, and (b) a pellet is re-suspended with a sterile PBS. The re-suspended pellet layer is placed on top of a ficoll density gradient medium (e.g., a density of 1.077 g/mL). A gradient is established by centrifuging at 1,500 rpm for 15 minutes. After centrifugation, cells are collected from a middle band of a centrifuged solution. A collected monolayer including cells is washed with PBS twice to obtain mesenchymal stem cells. The mesenchymal stem cells are re-suspended in DMEM for culturing, and are isolated from a culture.

The isolated mesenchymal stem cells are seeded at a density of $10^6$ cells per mL of DMEM supplemented with 10% FBS, 1% antibiotic solution and 2 mM L-Glutamine into a culture flask, and kept in a 5% $CO_2$ incubator. After 24 hours, non-adherent cells are removed from the culture flask, and a fresh media is added to the culture flask. The media is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per cm² for further culturing.

A second method for isolating and enriching mesenchymal stem cells from placental chorion is discussed below.

Full-term human placenta is obtained from a healthy mother after donor's written consent under a tissue collection protocol. With sterile procedures, fetal decidua's placental tissue is cut into pieces of 3 approximately 1 cm³ in size, is washed with PBS, and is digested with 1 mg/mL I type collagenase at 37° C. for 2 hours. After enzyme digestion, cells are separated via centrifugation over Ficoll-Hypaque separation medium at a 1.088 g/cm³ density gradient to remove unwanted cells. Cells which are wanted are collected, and are re-suspended for culture in the L-DMEM medium supplemented with 20% FBS, 10 U basic fibroblast growth factor, 2 mrnol/1 L-glutamine, 100 U/mL penicillin, and 100 pg/mL streptomycin. The cells are then seeded in 75 cm² flasks and are cultured in a 37° C., 5% $CO_2$ incubator with saturated humidity.

After 48 hours, non-adherent cells are removed from a culture medium by replacing the culture medium. Fresh medium is exchanged every 3 to 4 days. The cells from the culture medium are harvested by trypsinization (0.25% trypsin with 0.1% EDTA), subsequently the cells are passaged, and then cells are used during a fourth passage for co-culturing with mesenchymal stem cells from other sources.

A third method for isolating and enriching mesenchymal stem cells from placental chorion is discussed below.

Chorionic mesenchymal stem cells are isolated from term placenta. Chorionic sections of about 10 g are extensively minced. Minced chorionic sections are centrifuged at 550 g for 5 minutes. A pellet that is obtained from the centrifugation process is then haemolysed in a red blood cell lysis buffer. The red blood cell lysis buffer contains 155 mM $NH_4Cl$, 10 mM $KHCO_3$, 0.1 mM EDTA, at pH 8.0. After haemolysis, a mixture of the pellet and the red blood cell lysis buffer is centrifuged at 550 g for 5 minutes at room temperature. A pellet that is obtained from the centrifugation process is incubated at 37° C. in 0.05% Trypsin-EDTA solution for 10 minutes, is re-suspended twice in 50% a-MEM medium or 50% FBS, and is subjected to centrifugation at 550 g for 10 minutes at room temperature. Then, a pellet from the centrifugation process is plated in a-MEM medium supplemented with 20% FCS, 0.02% L-ascorbate-2-phosphate, 1% L-Glutamine, 0.5% penicillin/streptomycin, 0.5% Fungizone and 1% Tylosin. Cells are maintained in culture at 37° C. and 5% $CO_2$. Cell viability and numbers are determined by a Trypan Blue exclusion assay.

A fourth method for isolating and enriching mesenchymal stem cells from placental chorion is discussed below.

Chorion is separated from amnion by peeling them apart. The decidual tissue is scrapped mechanically, and is washed in Dulbecco's phosphate-buffered saline (DPBS) before being cut into small pieces (2×2 cm). The chorion are chopped into small pieces and are subjected in 0.5% trypsin-EDTA for 5 minutes, is followed by digestion with 0.3% collagenase I in 37° C. incubator for 20 to 30 minutes. Mobilized cells are then collected and are passed through a 100 μm cell strainer.

Mesenchymal stem cells are isolated and enriched from umbilical cord in a plurality of ways. A first method for isolating and enriching mesenchymal stem cells from umbilical cord is discussed below.

The surface of the umbilical cord is rinsed with sterile phosphate buffered saline to remove as much blood as possible. The length of the cord is estimated. The umbilical cord is placed in a sterile petri dish containing 100% alcohol for 30 seconds. The umbilical cord is manipulated in a sterile 10 cm petri dish, and the cord is cut into 3-5 cm long pieces using a sterile blade. Blood vessels are removed from each piece after incising the umbilical cord length wise. The umbilical cord tissue is placed into a sterile container and incubated in 0.1% Collagenase and dispase (7:1) solution for 2 hours at 37° C.

After incubation, 10% FBS containing DMEM is added to the sterile container to stop the Collagenase Type N and dispase activity. The umbilical cord pieces are crushed using serrated thumb forceps to release as many cells as possible into the solution, which is labeled as solution A. The umbilical cord tissue is placed into another sterile container, and the container is incubated in 0.25% Trypsin for 30 minutes at 37° C. After incubation, 10% FBS containing DMEM is added to the sterile container to stop the Collagenase Type N and dispase activity. The umbilical cord pieces are crushed using serrated thumb forceps to release as many cells as possible into the solution, which is labeled as solution B.

Both solutions A and B are mixed together, and are filtered through a 100 micron cells strainer. Filtrates from the 100 micron cells strainer are centrifuged using a centrifuge apparatus at 1,500 revolutions per minute (rpm) for 10 minutes. A centrifuged solution containing (a) supernatant is discarded, and (b) a pellet is re-suspended in DMEM for culturing. The isolated cells are seeded at a density of $10^6$ cells per mL of DMEM supplemented with 10% FBS, 1% antibiotic solution and 2 mM L-Glutamine into a culture flask, and kept in a 5% $CO_2$ incubator. After 24 hours, non-adherent cells are removed from the culture flask, and a fresh media is added to the culture flask. The media is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per $cm^2$ for further culturing.

A second method for isolating and enriching mesenchymal stem cells from the umbilical cord is discussed below.

The cord is disinfected in Betadine solution, and is followed by 100% ethanol wash and cleared off in normal saline. Using a sterile scalpel and forceps, the umbilical cord is dissected and unfolded, and the exposed arteries and vein are removed and discarded. The tissue is washed free of contaminating blood with normal saline throughout the process, and cut into 2-5 $mm^3$ pieces with a scalpel. The pieces are immersed in an enzymatic cocktail including 4 mg mL-1 Collagenase Type I and 1 mg mL-1 Hyaluronidase, and are incubated for 1 hour at 37° C. with gentle agitation. After that, 2.5% trypsin is added, and the pieces are further incubated for 30 minutes under same conditions. Digested suspension from the enzyme treatment is diluted in the ratio of 1:2 with PBS to reduce a viscosity of the suspension, and is passed through a 70 µm nylon mesh to obtain a single-cell suspension.

Cells are centrifuged at 500 g for 15 mm at 37° C., and a pellet is re-suspended in a medium containing 25% human albumin, HES 200/0.5 and citrate-phosphate-dextrose-adenine anticoagulant. Viable cells are counted using a trypan blue dye exclusion assay on a Neubauer hemocytometer. The isolated cells are seeded at a density of $10^6$ cells per mL of DMEM supplemented with 10% PBS, 1% antibiotic solution and 2 mM L-Glutamine into the culture flask and kept in a 5% $CO_2$ incubator. After 24 hours, non-adherent cells are removed from the culture flask, and a fresh media is added to the culture flask. The media is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per $cm^2$ for further culturing.

A third method for isolating and enriching mesenchymal stem cells from the umbilical cord is discussed below.

A whole umbilical cord is washed in sterile phosphate buffered saline (PBS) three times to remove red blood cells, is immersed in 70% ethanol for 30 seconds and then is immediately washed in PBS before further processing. Approximately 2-30 cm of the whole umbilical cord is taken for processing as a mixed umbilical cord, and approximately 6 cm of the whole umbilical cord is dissected to obtain artery, vein, and Wharton's jelly and cord lining. Explant cultures are obtained from each region which is weighed, are minced into small pieces (20 $mm^3$) with a sterile scalpel, and are placed into 6 well plates.

The explant cultures are grown in a culture medium containing Dulbecco's Modified Eagle's Medium (DMEM), foetal calf serum (FCS) (10%), and penicillin and streptomycin (P/S). Tissue explants are removed from culture after 21 days. Adherent cells are passaged upon reaching 70% confluence, and are reseeded at 5×103/$cm^2$ in either 25 El $cm^2$ or 75 O$cm^2$ tissue culture flasks. Viable cells are counted by trypan blue (Sigma) exclusion in a haemocytometer.

Mesenchymal stem cells that are isolated and enriched from two or more selected from (i) amniotic membrane, (ii) chorion, (iii) amniotic fluid, and (iv) umbilical cord are co-cultured in a medium under a hypoxic condition to obtain a mixture of co-cultured mesenchymal stem cells. Below are two examples provided for co-culturing of mesenchymal stem cells from different sources in a medium under hypoxic conditions. However, it is to be understood by a person having ordinary skill in the art that the specific examples are not meant to limit scope of the embodiments herein.

A first example for co-culturing of mesenchymal stem cells from amniotic membrane, amniotic fluid, chorion, and umbilical cord under hypoxic conditions is discussed below.

Co-Culture equal or unequal proportion of amniotic membrane, amniotic fluid, chorion, and umbilical cord derived mesenchymal stem cells (any two or more) in DMEM supplemented with 10% FBS, 2 mM L-glutamine and 1% antibiotic solution into the same culture flask and kept in a $CO_2$ incubator at 37° C., preferably under hypoxic condition (1-3% 02, 5% $CO_2$, 93% N2). In one embodiment, oxygen level can be lower than 1% too. The media is changed twice weekly. Once adherent cells reach the 70-80% confluence, the adherent cells (i.e., mesenchymal stem cells) are dissociated from the culture media with 0.25% trypsin. In a culture flask, 5,000-10,000 cells are seeded per $cm^2$ for further culturing.

A second example for co-culturing of mesenchymal stem cells from amniotic membrane, amniotic fluid, placental chorion, and umbilical cord under hypoxic conditions is discussed below.

An equal number of mesenchymal stem cells from amniotic membrane, amniotic fluid, placental chorionic, and umbilical cord that are isolated and enriched, are taken in DMEM supplemented with 10% FBS, antibiotic solution and glutamine in a culture flask and incubated in 5% $CO_2$ (hypoxy) incubator, at 37° C. under hypoxic condition (1-3% 02, 5% $CO_2$, 93% $N_2$). Non-adherent cells are removed from the culture medium. Fresh media is added every 24 hours. The culture medium is changed twice weekly, until the adherent cells reach the 70-80% confluence. Trypsin solution is added to harvest crop of dissociated mesenchymal stem cells obtained from amniotic membrane, amniotic fluid, placental chorionic and umbilical cord.

The safety efficacy and potency of a foetal polymix combination including a mixture of co-cultured mesenchymal stem cells which are obtained by co-culturing mesenchymal stem cells derived from at least two of a group including of (i) amniotic membrane, (ii) chorion, (iii) amniotic fluid, and (iv) umbilical cord in a medium under hypoxic conditions can be tested in an animal model. A medicament or a composition that includes the mixture of co-cultured mesenchymal stem cells is found to be effective in treating many diseases and disorders.

The efficacy and potency associated with the mixture of co-cultured mesenchymal stem cells or (Animal medical center) AMC derived from mesenchymal stem cells in treating diseases or disorders including diabetes mellitus, chronic kidney disease, liver cirrhosis, spinal cord injury, cardiac failure, retinitis pigmentosa and macular degeneration, autism, muscular dystrophies, non-union fractures, hair loss, knee osteoarthritis, Parkinson's disease, avascular necrosis, Alzheimer's disease, cerebral palsy, multiple sclerosis, anti-aging, and stroke are discussed below.

A) Diabetes Mellitus:

Sugar assessment tests in all animal groups were monitored, as in patients, by determination of blood sugar fasting, BSPL, blood sugar post prandial (BSPP), glycated hemoglobin (HBA1C) and inulin clearances. Overall animal outcome was assessed by determination of weight loss, hemodynamics (blood pressure), and survival, integration and differentiation into pancreatic cells. Selected animals in the various groups were followed for up to 28 days after the start of the study.

Sugar tests in 243 humans were monitored, as in patients, by determination of blood sugar levels and insulin clearance, creatinine, measurement of glomerular filtration rate (i.e., GFR for complications of kidney disorders) and hemodynamics (having blood pressure), fundoscopy (retinopathy complications) and EF (having CF complications). Overall human primary outcome was assessed by determination of blood sugar fasting (BSF) and BSPP. Secondary outcome was assessed by determination of HBA1C and insulin intake. Conclusion of the tests include (i) an improvement in BSF, (ii) an improvement in PPBS, (iii) an improvement in HBA1C, (iv) insulin dose reduction or patients went off insulin, (v) an improvement in creatinine, (vi) an improvement in hypertension, (vii) an improvement in nephropathy complications, (viii) an improvement in paraesthesias, and (ix) an improvement in neurological symptoms.

B) Chronic Kidney Disease:

Renal assessments in all animal groups were monitored, as in patients, by determination of creatinine, blood urea nitrogen (BUN) and glomerular filtration rate (GFR). Overall animal outcome was assessed by determination of weight loss, hemodynamics (blood pressure), and survival, integration and differentiation into renal cells. Selected animals in the various groups were followed for up to 28 days after the start of the study.

Renal assessments in 328 humans were monitored, as in patients, by determination of creatinine, BUN and GFR. Overall animal outcome was assessed by determination of weight loss, hemodynamics (blood pressure), and survival purposes, and their integration and differentiation into renal cells. Selected animals in the various groups were followed for up to 6 months after the start of the study. Conclusion of the tests include generates energy, helps in further deterioration of kidney stage, an improvement in creatinine levels (i.e., creatinine decreases), an improvement in GFR levels (i.e., GFR increases), increases appetite ultimately patient regains lost weight, and an improvement in complications like diabetes (control in BSF and BSPP values, reduces intake of insulin dose) and hypertension (back to normal or reduces blood pressure).

C) Liver Cirrhosis:

LFT assessments in all animal groups were monitored, as in patients, by determination of bilirubin, total proteins, and a ratio of albumin and globulin. Overall animal outcome was assessed by determination of weight loss, hemodynamics (blood pressure), and survival, integration and differentiation into liver cells. Selected animals in the various groups were followed for up to 28 days after the start of the study.

LFT assessments in all 323 humans were monitored, as in patients, by determination of bilirubin, total proteins, and a ratio of albumin and globulin. Overall outcome was assessed by determination of weight loss, hemodynamics (blood pressure), and survival, integration and differentiation into liver cells. Selected animals in the various groups were followed for up to 6 months after the start of the study. Conclusion of the tests include an improvement seen in ascites, a decrease in tapping for ascites or a complete loss of ascites formation, an increase in albumin levels, a decrease in globulin levels, and an improvement in total proteins.

D) Spinal Cord Injury:

Physical assessments in all animal groups were monitored, as in patients, by determination of bowel bladder control, urinary sensation, and a sense of touch. Overall animal outcome was assessed by determination of weight loss, hemodynamics (blood pressure), and survival, integration and differentiation into sensory cells. Selected animals in the various groups were followed for up to 28 days after the start of the study.

Physical assessments in all 173 humans were monitored, as in patients, by determination of bowel bladder control, urinary sensation, and a sense of touch. Overall outcome was assessed by determination of weight loss, hemodynamics (blood pressure), and survival, integration and differentiation into sensory cells. Selected animals in the various groups were followed for up to 6 months after the start of the study. Conclusion of the assessments includes an improvement in bowel bladder control, an improvement in urinary sensation, and an improvement in sense of touch.

E) Cardiac Failure:

Cardiac function assessments in 179 humans were monitored, as in patients, by determination of an ejection fraction, breathlessness and 2D-echocardiogram. Overall outcome was assessed by determination of weight loss, hemodynamics (blood pressure), and survival, integration and differentiation into cardiac muscle cells. Selected humans in the various groups were followed for up to 6 months after the start of the study. Conclusion of the assessments includes increase in the ejection fraction, loss of breathlessness, and an increase in ability to climb stairs and walking longer distances was also increased.

F) Retinitis Pigmentosa and Macular Degeneration:

Ophthalmology assessments in 76 male and female patients were monitored, as in patients, by determination of fundoscopy, an eye examination and a vision test. Overall outcome was assessed by determination of weight loss, hemodynamics (blood pressure), and survival, integration and differentiation into eye retina cells. Selected humans in the various groups were followed for up to 6 months after the start of the study. Conclusion of the assessments includes improvement in a visual field (visual field expands), an improvement in a vision quality, and helps in prevention from further deterioration.

G) Autism:

Neurological assessments in 316 male and female patients were monitored, as in patients, by determination of speech, language, behavior, social, cognitive and physical criteria. The main criteria for evaluation were ATEC (i.e., Autism treatment evaluation checklist). Overall outcome was assessed by determination of weight loss, hemodynamics (blood pressure), and survival, integration and differentiation into neural cells. Selected humans in the various groups were followed for up to 6 months after the start of the study. Conclusion of the assessments include an improvement in speech, an improvement in communication, an improvement in health and physical condition, an improvement in behavior, an improvement in cognitive awareness, an improvement in language, and an improvement in ATEC score.

H) Muscular Dystrophies:

Physical assessments in 303 male and female patients were monitored, as in patients, by determination of a muscular tone, a grade, Gower's time, rigidity and spasticity. In Facioscapulohumeral muscular (FSH) dystrophy bicep size and muscle bulk is determined. Overall outcome was assessed by determination of weight loss, hemodynamics (blood pressure), and survival, integration and differentiation into muscles. Selected humans in the various groups were followed for up to 6 months after the start of the study. Conclusion of the assessments includes an improvement in EMG studies, prevention from further deterioration is observed, in cases like FSH muscular dystrophy muscle growth is observed. In Duchene muscular dystrophy (DMD) an increase in creatine kinase (CPK) levels are seen, and Bedridden and wheel chair bound limb-girdle muscular dystrophy (LGMD) and DMD patients were able to walk with the help of splints.

I) Non-Union Fractures:

Imaging test assessments in 354 male and female patients were monitored, as in patients, by determination of degree and grade of healing fracture, amount of sensation of pain while walking, standing, and climbing stairs if fracture is located at LE.

Overall outcome was assessed by determination of weight loss, hemodynamics (blood pressure), and survival, integration and differentiation into cartilage or bone formation. Selected humans in the various groups were followed for up to 6 months after the start of the study. Conclusion of the assessments include improvement in healing fracture, significant pain relief at rest, and noteworthy pain-relief while walking, standing, climbing stairs if fracture is located at LE.

J) Hair Loss:

Physical assessments in 211 male and female patients were monitored, as in patients, by determination of degree and grade of hair loss. Overall outcome was assessed by determination of weight loss, hemodynamics (blood pressure), and survival, integration and differentiation into hair cells formation. Selected humans in the various groups were followed for up to 6 months after the start of the study. Conclusion of the assessments includes hair re-growth, greying of white hair was also observed, and hair-line re-growth was observed.

K) Knee Osteoarthritis:

MRI cartigram and physical assessments in 211 male and female patients were monitored, as in patients, by determination of grade of knee Osteoarthritis. Overall outcome was assessed by determination of weight loss, hemodynamics (blood pressure), and survival, integration and differentiation into cartilage or bone formation. Selected humans in the various groups were followed for up to 6 months after the start of the study. Conclusion of the assessments includes an improvement in walking, relief in pain, and an improvement in climbing stairs, an improvement in sitting and standing, and regeneration of cartilage was observed.

L) Parkinson's Disease:

Physical assessments in 265 male and female patients were monitored, as in patients, by determination of grade of Parkinson's disease. Overall outcome was assessed by determination of weight loss, hemodynamics (blood pressure), and survival, integration and differentiation into neural cells. Selected humans in the various groups were followed for up to 6 months after the start of the study. Conclusion of the assessments include loss of tremors in both upper extremities (UE) and lower extremities (LE) at rest, loss of tremors while walking writing, etc., gait improved, no problem with buttoning, eating, etc. thereby daily routine activities were improved, motor symptoms like shaking, rigidity, slowness of movement and difficulty with walking and gait were improved, an improvement seen in cognitive and behavioral symptoms—Dementia attention deficit and memory loss, and an improvement in sensory, and sleep and emotional symptoms.

M) Avascular Necrosis (AVN):

Imaging test studies in 211 male and female patients were monitored, as in patients, by determination of grade of AVN of hip, pain relief and resistance while sleeping, walking, and standing, etc. Overall outcome was assessed by determination of weight loss, hemodynamics (blood pressure), and survival, integration and differentiation into nerve cells. Selected humans in the various groups were followed for up to 6 months after the start of the study. Conclusion of the assessments include relieve in pain, stops progression of bone damage, and a regeneration of cartilage.

N) Alzheimer's Disease (AD):

Neurological examinations in 238 male and female patients were monitored, as in patients, by determination of mini-temporal examination and grade of AD. Overall outcome was assessed by determination of weight loss, hemodynamics (blood pressure), and survival, integration and differentiation into neuronal cells. Selected humans in the various groups were followed for up to 6 months after the start of the study. Conclusion of the assessments include an improvement in memory, an improvement in attentiveness, an improvement in communication skills, an improvement in independent activities, and an improvement in speech.

O) Cerebral Palsy:

Neurological examinations in 289 male and female patients were monitored, as in patients, by determination of electromyography (EMG) studies, spasticity, rigidity and gait. Overall outcome was assessed by determination of weight loss, hemodynamics (blood pressure), and their survival, integration and differentiation into neuronal cells. Selected humans in the various groups were followed for up to 6 months after the start of the study. Conclusion of the examination includes an improvement in spasticity, an improvement in ataxia, an improvement in cognitive function, an improvement in speech, an improvement in gait, and an improvement in communication.

P) Multiple Sclerosis:

Neurological examinations in 170 male and female patients were monitored, as in patients, by determination of MRI and physical assessments like weakness, tingling, numbness, and blurred vision. Overall outcome was assessed by determination of weight loss, hemodynamics (blood pressure), and their survival, integration and differentiation into neuronal cells. Selected humans in the various groups were followed for up to 6 months after the start of the study. Conclusion of the examination includes an improvement in muscle strength, an improvement in sensory symptoms, an improvement in problems in walking, an improvement in problems in bladder or bowel control, an improvement in speech, and an improvement in ataxia.

Q) Anti-Aging:

Physical assessments in 163 male and female patients were monitored, as in patients, by determination of facial lines, wrinkles etc. Selected humans in the various groups were followed for up to 6 months from start. Conclusion of the assessment includes a loss of wrinkles, facial lines are seen and greying of white hair was observed.

R) Stroke:

Imaging test assessments in 263 male and female patients were monitored. Overall outcome was assessed by determination of a weight loss, hemodynamics (blood pressure), and their survival, integration and differentiation into neuronal cells. Selected humans in the various groups were followed for up to 6 months after the start of the study. Conclusion of the assessment includes generates energy, helps in further deterioration of paralysis or numbness of face, arms, or legs especially on one side of the body, patients suffering from trouble speaking or understanding speech were benefitted, an improvement in vision for those who have trouble seeing in one or both eyes, a loss of breathlessness up to a significant extent, an improvement in some symptoms like dizziness, trouble walking, loss of balance or coordination and unexplained falls, regains consciousness, and an improvement in headache.

A product or a medicament or a composition including a mixture of mesenchymal stem cells that are obtained by co-culturing mesenchymal stem cells from various sources in a medium under hypoxic conditions is administered into subjects via different routes. A route for administering the medicament or the composition varies depends on a disease or a disorder type. For example, T-75 flasks of amnion MSCs, umbilical cord MSCs and chorionic MSCs are cultured together, then are mixed and are grown together. After that, appropriate numbers of chorionic, umbilical cord, and amnion mesenchymal stem cells are combined at preferably a defined ratio for making a medicament.

The dose of the medicament may include a composition of MSCs selected from a group including of: (a) chorionic MSCs and amnion MSCs, (ii) umbilical cord MSCs and chorionic MSCs, (c) amnion MSCs and umbilical cord MSCs, and (d) chorionic MSCs, amnion MSCs and umbilical cord MSCs. A total number of each cell type is administered for studies or treating diseases or disorders in subjects may be about 1.6 million MSCs/kg body weight of subject. Physical appearance of each vial measures approximately 1 mL. Then, in one embodiment, the medicament is administered into patients via following routes that differ depends on diseases or disorders type as described below.

Cerebral palsy, autism, Parkinson's disease, multiple sclerosis, Alzheimer's and other neurodegenerative disorders are treated with a combination of intravenous (IV) and intra-thecal (IT) injections. Diabetes, stroke, spinal cord injury, multiple sclerosis, stroke, cardiac failure and cardiomyopathies, liver cirrhosis, kidney disorders are treated via intravenous injection. Avascular necrosis and osteoarthritis are treated with intra-articular (IA) injection, also accompanied by platelets and calcium for formation of a gel based mesh, and infused by core decompression if necessary.

Muscular dystrophy is treated with intra-muscular (IM) injection and intravenous routes. Hair-loss and local (aesthetic) anti-aging are treated via local route of administration either by derma rollers or mesoguns. Vitiligo and depigmentation or hypopigmentation are treated via local route of administration either by artificial induction of blisters by liquid nitrogen, or dermabrasion. Retinitis pigmentosa and macular degeneration are treated with peri-orbital or intra-vitreal or retrobular routes.

Examples of protocols or methods for administering a medicament or a composition including a mixture of co-cultured mesenchymal stem cells into a subject via different routes are discussed below. However, it is to be understood by a person having ordinary skill in the art that the medicament or the composition can also be administered using other protocols that are known in the art.

A first example method for administering a medicament into a knee osteoarthritis patient via intra-articular (IA) route is discussed below.

The injection area is waxed with ethyl alcohol and beta-dine. A needle (e.g., a spinal needle) is inserted in the intra-articular knee joint space such that the needle should not touch muscle or bone with the help of C-arm guidance or an ultra sonography. Sample A containing calcium carbonate and sample B containing platelet are aspirated, and are mixed thoroughly. After 5 minutes the aspirate of sample A and sample B are introduced in the hip joint through the needle. After another 5 minutes, a sample C containing a combination of AMC mesenchymal stem cells is taken from vial C in a syringe. The sample C is infused via same route, and the needle is removed. Extension or flexion is done 7-10 times after the spinal needle is removed. One knee is operated at a time. The operated knee is given more rest for a period of 1 month as much as possible. Lifting heavy weights should be avoided as well.

A second example method for administering a medicament into an avascular necrosis patient via intra-articular (IA) route is discussed below.

The injection area is waxed with ethyl alcohol and beta-dine. A needle (e.g., a spinal needle) is inserted in the intra-articular knee joint space such that the needle should not touch muscle or bone with the help of C-arm guidance or an ultra sonography. Sample A containing calcium carbonate and sample B containing platelet are aspirated, and are mixed thoroughly. After 5 minutes the aspirate of sample A and sample B are introduced in the hip joint through the needle. After another 5 minutes, a sample C containing a mixture of co-cultured mesenchymal stem cells is taken from vial C in a syringe. The sample C is infused via same route, and the needle is removed.

A third example method for administering a medicament into a patient via intravenous (IV) route is discussed below.

A thermocol container containing mesenchymal stem cells is unpacked. Aluminum foil is removed from the container. The container is brought to a room temperature. Vial and type of cells is checked with respect to the COA. The vial is taken in between palms to mix the mesenchymal stem cells thoroughly, and is brought to room temperature. The mesenchymal stem cells are drawn in a syringe using 21 no needle. The patient's arm is prepared for intravenous injection. A site of injection is cleaned with spirit. The patient's vein is secured with a scalp vein set. A syringe is attached to the 23 no scalp. A rate of transfusion may be 0.5 mL of stem cells per minute. The patient is monitored properly during transfusion. After a complete vial is injected approximate 5 mL normal saline is flushed. The patient is monitored for at least 4 hours after the transfusion for any reactions. Any inconvenience caused is informed immediately to a concerned authority. Adverse reactions expected during transfusion including tachycardia, and after transfusion include fever, chills, tiredness and occasionally thrombophlebitis.

A fourth example method for administering a medicament into a patient via intra-thecal route is discussed below.

A thermocol container containing mesenchymal stem cells is unpacked. Aluminum foil is removed from the container. The container is brought to a room temperature. The vial and type of cells is checked with respect to the COA. The vial is taken in between palms to mix the mesenchymal stem cells thoroughly, and is brought to room temperature. The mesenchymal stem cells are drawn in a syringe using 22 no needle. Before injection, patient's skin is disinfected and numbed with local anesthesia so that the patient does not feel pain of the intra-thecal injection. The site of the injection is cleaned with spirit. The 23 No. spinal needle is attached to the spine.

A rate of transfusion may be 0.5 mL of stem cells per minute. The patient is monitored properly during transfusion. After a complete vial is injected approximately 5 mL normal saline is flushed. The patient is monitored for at least 4 hours after the transfusion for any reactions. Any inconvenience caused is informed immediately to a concerned authority. Adverse reactions expected during transfusion include tachycardia, and after transfusion including fever, chills, tiredness and occasionally thrombophlebitis.

A fifth example method for administering a medicament into a patient via intramuscular route is discussed below.

A thermocol container containing mesenchymal stem cells is unpacked. Aluminum foil is removed from the container. The container is brought to a room temperature. The vial and type of cells is checked with respect to the COA. The vial is taken in between palms to mix the mesenchymal stem cells thoroughly, and is brought to room temperature. The mesenchymal stem cells are drawn in a syringe using no needle. A patient is prepared for intramuscular injection. An injection site is cleaned with spirit or alcohol swab, and the site is permitted to dry. An alcohol swab or a clean gauze is kept ready to cover the site once the needle is pulled out from the site. The syringe is held at a 90 degree angle to the site. The needle is inserted straight into the skin with a 23 no needle. The mesenchymal stem cells are slowly injected until the syringe is empty. The needle is quickly removed at the angle in which it was injected. The alcohol swab or the clean gauze is placed at the injection site, and pressure is applied on the injection site for 30 seconds to 1 minute. The patient is monitored for at least 4 hours after the transfusion for any reactions. Any inconvenience caused is informed immediately to a concerned authority. Adverse reactions expected during transfusion include tachycardia, and after transfusion including fever, chills, tiredness and occasionally thrombophlebitis.

A sixth example method for administering a medicament into a patient via intravitreal route is discussed below.

Recent test reports along with complete case history of patients are obtained to ascertain eligibility. Test reports include basic eye checkup including vision, tension, and pressure, best corrected visual acuity, fundus photograph, visual field test (30-2 or appropriate), OCT evaluation of macula, complete Electroretinogram (ERG), and/or visual evoked potential (VEP). Based on the test reports a suitable response is given. After confirming eligibility, bone marrow aspiration is done, and a dose is planned for the following day. The eye which is affected more is treated first. The following day, an intravitreal procedure is performed on an OPD basis. The post-operative patient has to visit a retina specialist on day 1 and day 4 for a routine checkup. A similar procedure is repeated for another eye after a month interval.

A seventh example method for administering a medicament into a patient via a derma roller is discussed below.

The operating area is cleaned and prepared. Local anesthesia is applied for 45 minutes to 1 hour. After 1 hour, the area is cleaned with savlon, betadine and saline. A dropper is used to drop stem cells on the affected area. The derma roller is rolled over in either a fan shape or crisscross pattern until the required rounds. The cleansing protocol is again repeated. A superficial antibiotic is applied, and sent for the derma roller. Follow up is performed after 4-6 weeks.

An eighth example method for administering a medicament into a patient via mesotherapy is discussed below.

The operating area is cleaned with spirit. A solution is loaded in the mesogun. The mesogun is used with setting. A topical antibiotic is used in the end. Any other medication or oral antibiotic may not be required. Follow up is performed in 4 weeks. Depending on a disorder and a stage, processes like peri-orbital, retrobulbar, local infusions, dermabrasions etc. may also be adopted for optimal results.

In one embodiment, a stable composition of young stem cells for regenerative wound healing with neuro-rescue effects is provided. The composition includes an equal number of amniotic membrane, amniotic fluid, chorionic, and umbilical cord derived mesenchymal stem cells (any two or more) in DMEM supplemented with 10% FBS, 2 mM L-glutamine and 1% antibiotic solution into the same culture flask and kept in a $CO_2$ incubator under hypoxic conditions (1-3% $O_2$, 5% $CO_2$, 93% $N_2$). In one embodiment, a composition including a mixture of co-cultured mesenchymal stem cells after co-culturing is stable if stored at −196° C. potentially for indefinite periods of time (e.g., days, months, years, decades etc.) provided the storage of cells are retained under cryogenic conditions. Co-culture of mesenchymal stem cells includes, but is not limited to, (a) amniotic MSCs (1.33 million cells/kg body weight) at 1-100% of the total cell population, (b) chorionic MSCs (1.33 million cells/kg body weight) at 1-100% of the total cell population, and (c) umbilical cord MSCs (1.33 million cells/kg body weight) at 1-100% of the total cell population. This composition is co-cultured preferably, but is not limited, to hypoxic conditions at the oxygen concentration of approximately 1-3%, carbon dioxide concentration of approximately 5%, and nitrogen concentration of approximately 93%. A composition including co-cultured MSCs is stored in phosphate buffer (90% by volume) and plasmolyte solution (10% by volume) at the pH of 7.2 to 7.4. A shelf life of the composition is 24 hours if kept at 4° C.

FIG. 1 is a flow diagram illustrating a method for isolating, enriching, and co-culturing of a foetal polymix according to an embodiment herein. The method includes, in step 102, two or more components of mesenchymal stem cells derived from any of a placenta, amniotic membrane, chorion, amniotic fluid, and umbilical cord are provided in a medium under any of a hypoxic and a normoxic condition. In step 104, the mesenchymal stem cells are provided as an injectable composition.

Figure 2:
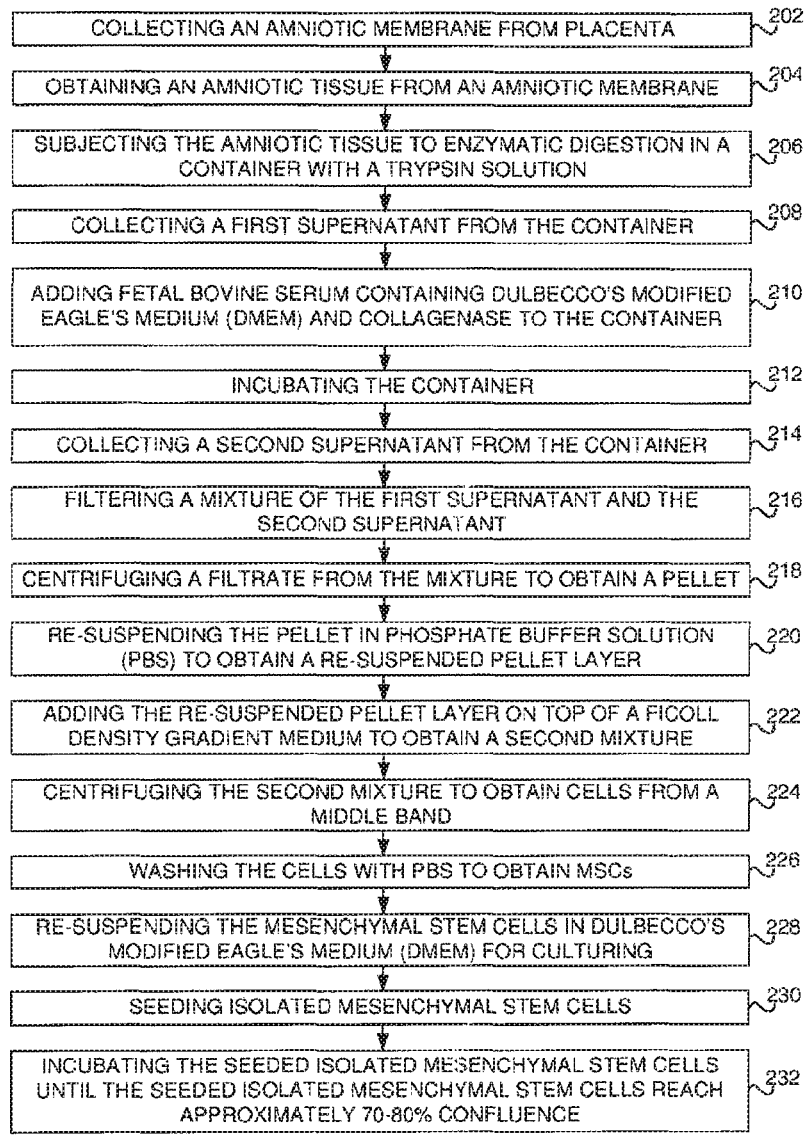
FIG. 2 is a flow diagram illustrating a method for isolating mesenchymal stem cells from a placental amniotic membrane according to an embodiment herein.

FIG. 2 is a flow diagram illustrating a method for isolating mesenchymal stem cells from a placental amniotic membrane according to an embodiment herein. The method includes, in step 202, an amniotic membrane is collected from placenta. In step 204, an amniotic tissue is obtained from the amniotic membrane. In step 206, the amniotic tissue is subjected to enzymatic digestion in a container with a trypsin solution. In step 208, a first supernatant is collected from the container. In step 210, fetal bovine serum containing Dulbecco's Modified Eagle's Medium (DMEM) and collagenase are added to the container. In step 212, the container is incubated. In step 214, a second supernatant is collected from the container. In step 216, a mixture of the first supernatant and the second supernatant is filtered. In step 218, a filtrate from the mixture is centrifuged to obtain a pellet.

In step 220, the pellet is re-suspended in phosphate buffer solution (PBS) to obtain a re-suspended pellet layer. In step 222, the re-suspended pellet layer is added on top of a ficoll density gradient medium to obtain a second mixture. In step 224, the second mixture is centrifuged to obtain cells from a middle band. In step 226, the cells are washed with PBS to obtain mesenchymal stem cells (MSCs). In step 228, the mesenchymal stem cells are re-suspended in Dulbecco's Modified Eagle's Medium (DMEM) for culturing. In step 230, isolated mesenchymal stem cells are seeded. In step 232, the seeded isolated mesenchymal stem cells are incubated until the seeded isolated mesenchymal stem cells reach approximately 70-80% confluence.

Figure 3:
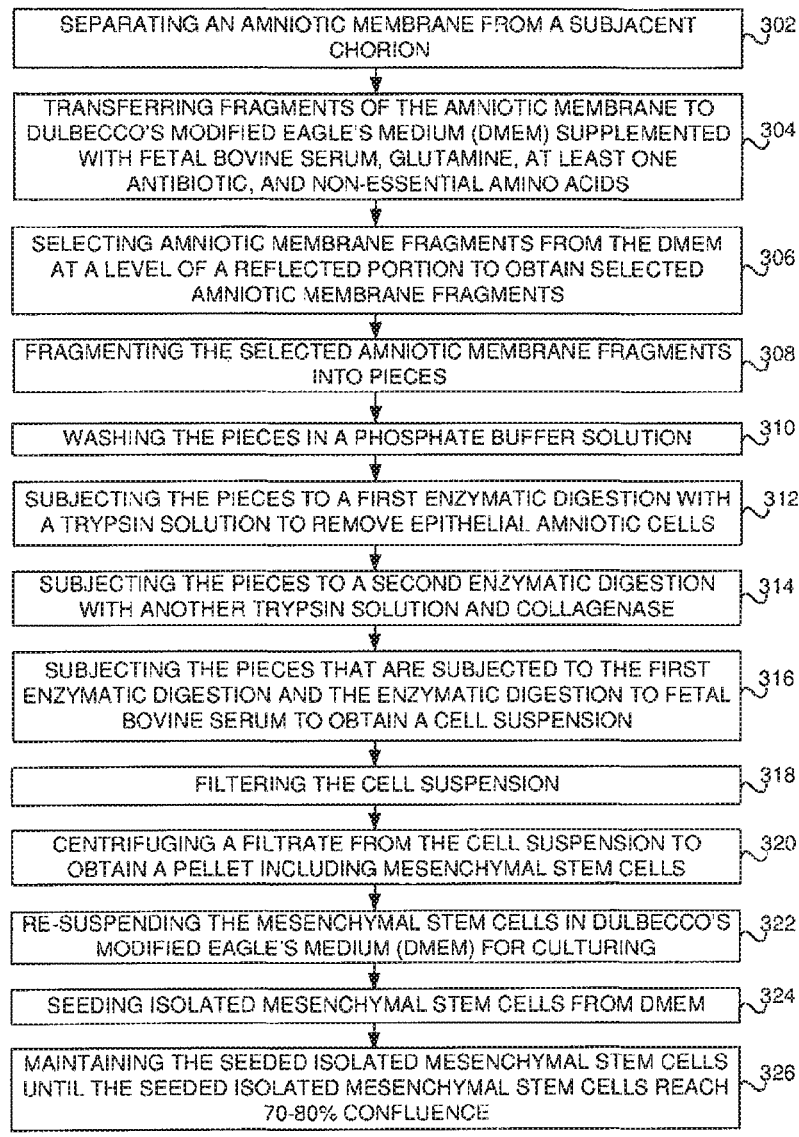
FIG. 3 is a flow diagram illustrating a method for isolating mesenchymal stem cells according to an embodiment herein.

FIG. 3 is a flow diagram illustrating a method for isolating mesenchymal stem cells according to an embodiment herein. The method includes, in step 302, an amniotic membrane is separated from a subjacent chorion. In step 304, fragments of the amniotic membrane are transferred to Dulbecco's Modified Eagle's Medium (DMEM) supplemented with fetal bovine serum, glutamine, at least one antibiotic, and non-essential amino acids. In step 306, amniotic membrane fragments are selected from the DMEM at a level of a reflected portion to obtain selected amniotic membrane fragments. In step 308, the selected amniotic membrane fragments are fragmented into pieces. In step 310, the pieces are washed in a phosphate buffer solution. In step 312, the pieces are subjected to a first enzymatic digestion with a trypsin solution to remove epithelial amniotic cells. In step 314, the pieces are subjected a second enzymatic digestion with another trypsin solution and collagenase. In step 316, the pieces that are subjected to the first enzymatic digestion and the enzymatic digestion to fetal bovine serum to obtain a cell suspension. In step 318, the cell suspension is filtered. In step 320, a filtrate from the cell suspension is centrifuged to obtain a pellet including mesenchymal stem cells.

In step 322, the mesenchymal stem cells are re-suspended in Dulbecco's Modified Eagle's Medium (DMEM) for culturing. In step 324, isolated mesenchymal stem cells are seeded from DMEM. In step 326, the seeded isolated mesenchymal stem cells are maintained until the seeded isolated mesenchymal stem cells reach 70-80% confluence.

Figure 4:
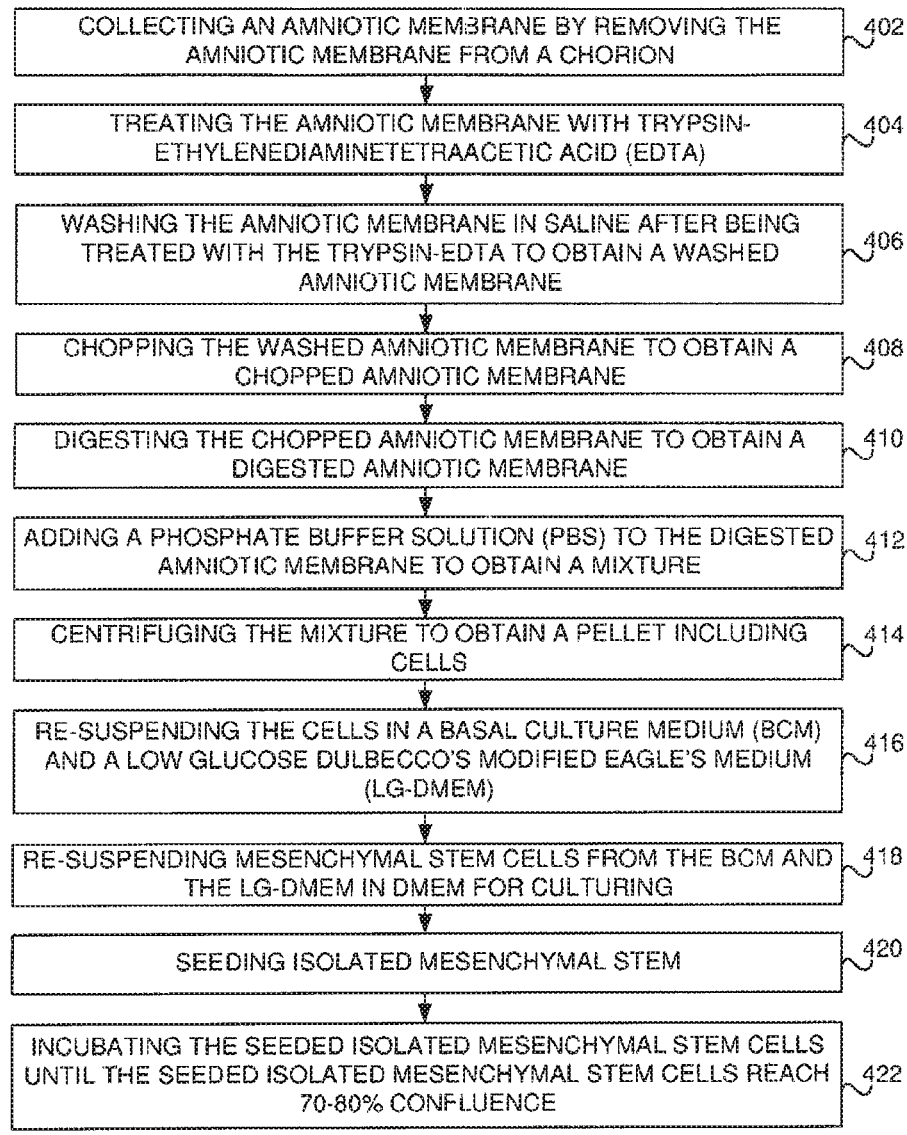
FIG. 4 is a flow diagram illustrating a method for isolating mesenchymal stem cells according to an embodiment herein.

FIG. 4 is a flow diagram illustrating a method for isolating mesenchymal stem cells according to an embodiment herein. The method includes, in step 402, an amniotic membrane is collected by removing the amniotic membrane from a chorion. In step 404, the amniotic membrane is treated with trypsin-ethylenediaminetetraacetic acid (EDTA). In step 406, the amniotic membrane is washed in saline after being treated with the trypsin-EDTA to obtain a washed amniotic membrane. In step 408, the washed amniotic membrane is chopped to obtain a chopped amniotic membrane. In step 410, the chopped amniotic membrane is digested to obtain a digested amniotic membrane. In step 412, a phosphate buffer solution (PBS) is added to the digested amniotic membrane to obtain a mixture. In step 414, the mixture is centrifuged to obtain a pellet including cells.

In step 416, the cells are re-suspended in a basal culture medium (BCM) and a low glucose Dulbecco's Modified Eagle's Medium (LG-DMEM). In step 418, mesenchymal stem cells are re-suspended from the BCM and the LG-DMEM in DMEM for culturing. In step 420, isolated mesenchymal cells are isolated. In step 422, the seeded isolated mesenchymal stem cells are incubated until the seeded isolated mesenchymal stem cells reach 70-80% confluence.

Figure 5:
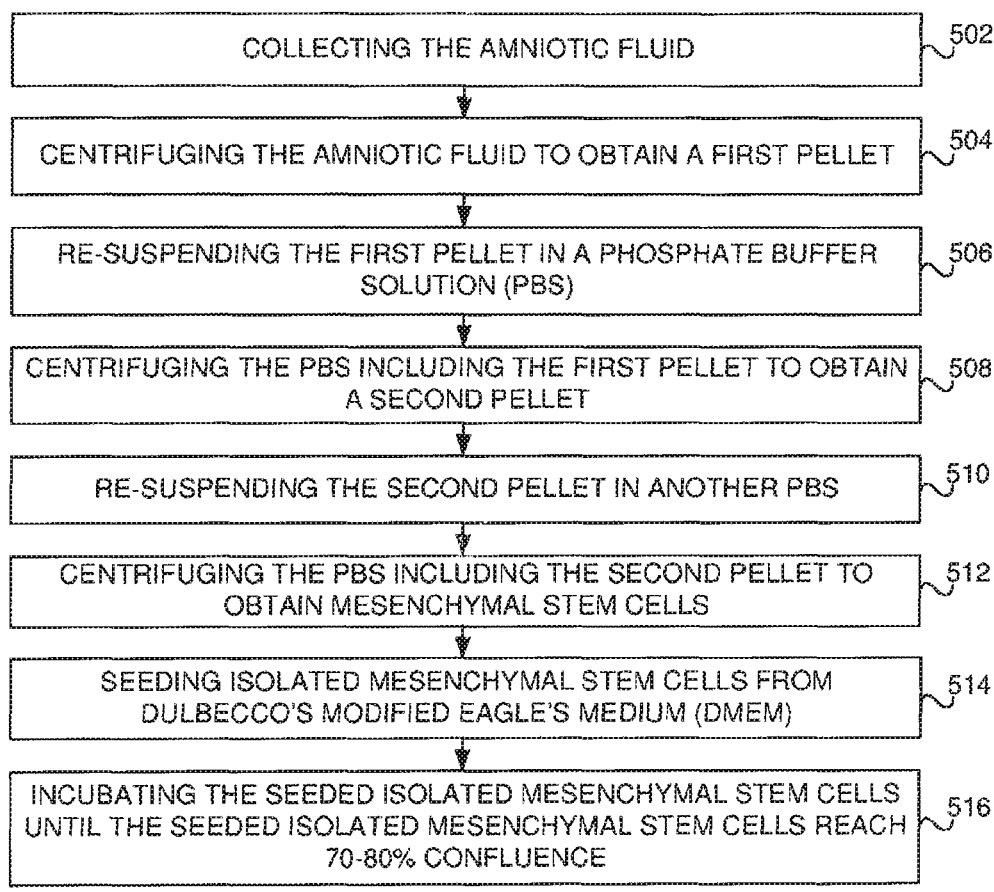
FIG. 5 is a flow diagram illustrating a method for isolating mesenchymal stem cells from amniotic fluid according to an embodiment herein.

FIG. 5 is a flow diagram illustrating a method for isolating mesenchymal stem cells from amniotic fluid according to an embodiment herein. In step 502, the amniotic fluid is collected. In step 504, the amniotic fluid is centrifuged to obtain a first pellet. In step 506, the first pellet is re-suspended in a phosphate buffer solution (PBS). In step 508, the PBS including the first pellet is centrifuged to obtain a second pellet. In step 510, the second pellet is re-suspended in another PBS. In step 512, the PBS including the second pellet is centrifuged to obtain mesenchymal stem cells.

In step 514, isolated mesenchymal stem cells are seeded from Dulbecco's Modified Eagle's Medium (DMEM). In step 516, the seeded isolated mesenchymal stem cells are incubated until the seeded isolated mesenchymal stem cells reach 70-80% confluence.

Figure 6:
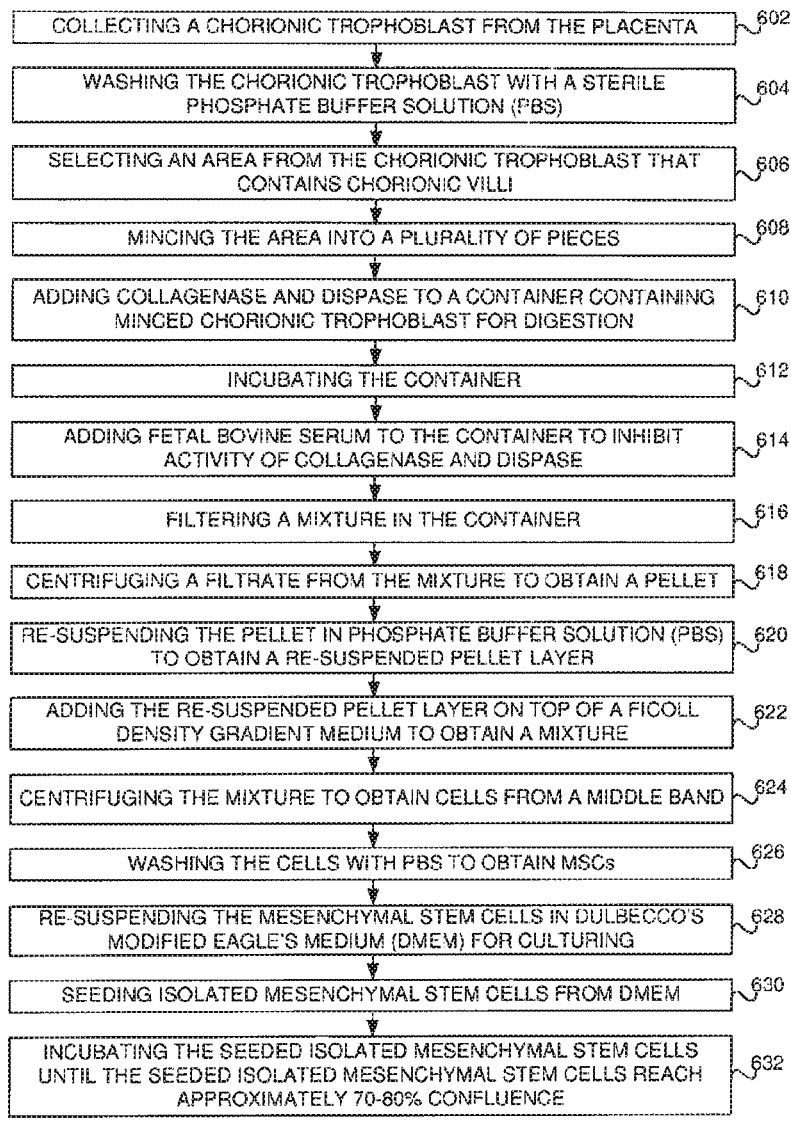
FIG. 6 is a flow diagram illustrating a method for isolating mesenchymal stem cells from a placenta according to an embodiment herein.

FIG. 6 is a flow diagram illustrating a method for isolating mesenchymal stem cells from a placenta according to an embodiment herein. The method includes, in step 602, a chorionic trophoblast is collected from the placenta. In step 604, the chorionic trophoblast is washed with a sterile phosphate buffer solution (PBS). In step 606, an area is selected from the chorionic trophoblast that contains chorionic villi. In step 608, the areas is minced into a plurality of pieces. In step 610, collagenase and dispase are added to a container containing minced chorionic trophoblast for digestion. In step 612, the container is incubated. In step 614, fetal bovine serum is added to the container to inhibit activity of collagenase and dispase. In step 616, a mixture is filtered in the container. In step 618, a filtrate is centrifuged from the mixture to obtain a pellet.

In step 620, the pellet is re-suspended in another PBS to obtain a re-suspended pellet layer. In step 622, the re-suspended pellet layer is added on top of a ficoll density gradient medium to obtain a mixture. In step 624, the mixture is centrifuged to obtain cells from a middle band. In step 626, the cells are washed with PBS to obtain mesenchymal stem cells. In step 628, the mesenchymal stem cells are re-suspended in Dulbecco's Modified Eagle's Medium (DMEM) for culturing. In step 630, isolated mesenchymal stem cells are seeded from DMEM. In step 632, the seeded isolated mesenchymal stem cells are incubated until the seeded isolated mesenchymal stem cells reach 70-80% confluence.

Figure 7:
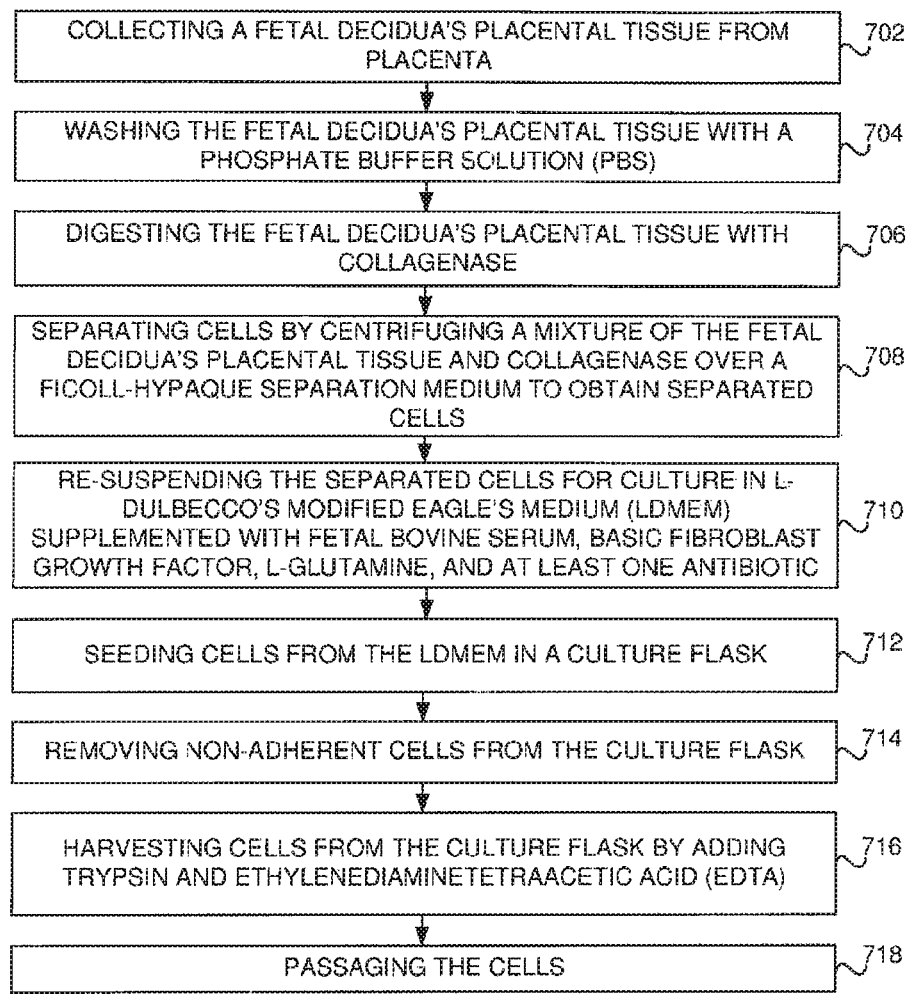
FIG. 7 is a flow diagram illustrating a method for isolating mesenchymal stem cells from a placenta according to an embodiment herein.

FIG. 7 is a flow diagram illustrating a method for isolating mesenchymal stem cells from a placenta according to an embodiment herein. The method includes, in step 702, a fetal decidua's placental tissue is collected from placenta. In step 704, the fetal decidua's placental tissue is washed with a phosphate buffer solution (PBS). In step 706, the fetal decidua's placental tissue is digested with collagenase. In step 708, cells are separated by centrifuging a mixture of the fetal decidua's placental tissue and collagenase over a Ficoll-Hypaque separation medium to obtain separated cells.

In step 710, the separated cells are re-suspended for culture in L-Dulbecco's Modified Eagle's Medium (LD-MEM) supplemented with fetal bovine serum, basic fibroblast growth factor, L-glutamine, and at least one antibiotic. In step 712, cells are seeded from the LDMEM in a culture flask. In step 714, non-adherent cells are removed from the culture flask. In step 716, cells are harvested from the culture flask by adding trypsin and ethylenediaminetetraacetic acid (EDTA). In step 718, the cells are passaged.

Figure 8:
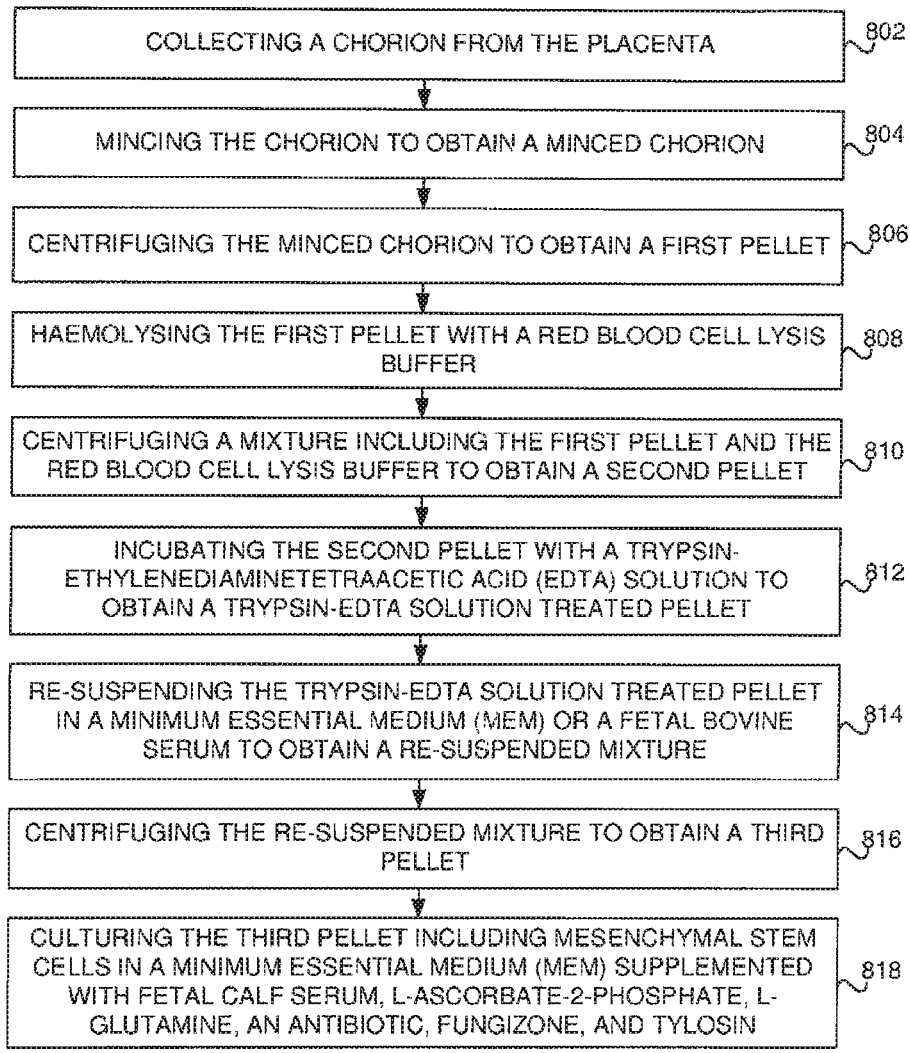
FIG. 8 is a flow diagram illustrating a method for isolating mesenchymal stem cells from a placenta according to an embodiment herein.

FIG. 8 is a flow diagram illustrating a method for isolating mesenchymal stem cells from a placenta according to an embodiment herein. The method includes, in step 802, a chorion is collected from the placenta. In step 804, the chorion is minced to obtain a minced chorion. In step 806, the minced chorion is centrifuged to obtain a first pellet. In step 808, the first pellet is haemolysed with a red blood cell lysis buffer. In step 810, a mixture including the first pellet and the red blood cell lysis buffer are centrifuged to obtain a second pellet. In step 812, the second pellet is incubated with a trypsin-ethylenediaminetetraacetic acid (EDTA) solution to obtain a trypsin-EDTA solution treated pellet.

In step 814, the trypsin-EDTA solution treated pellet is re-suspended in a minimum essential medium (MEM) or a fetal bovine serum to obtain a re-suspended mixture. In step 816, the re-suspended mixture is centrifuged to obtain a third pellet. In step 818, the third pellet including mesenchymal stem cells are cultured in a minimum essential medium (MEM) supplemented with fetal calf serum, L-ascorbate-2-phosphate, L-Glutamine, an antibiotic, fungizone, and tylosin.

Figure 9:
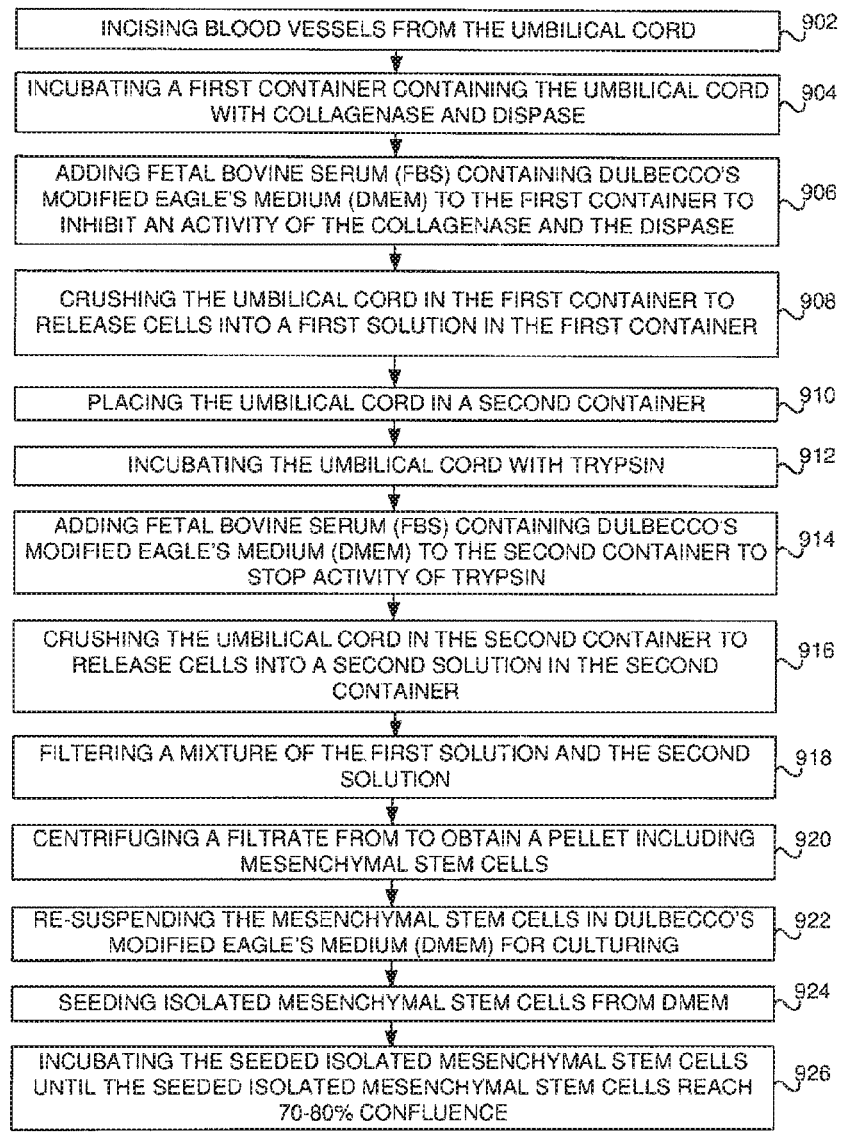
FIG. 9 is a flow diagram illustrating a method for isolating mesenchymal stem cells from an umbilical cord according to an embodiment herein.

FIG. 9 is a flow diagram illustrating a method for isolating mesenchymal stem cells from an umbilical cord according to an embodiment herein. The method includes, in step 902, blood vessels are incised from the umbilical cord. In step 904, a first container containing the umbilical cord is incubated with collagenase and dispase. In step 906, fetal bovine serum (FBS) containing Dulbecco's Modified Eagle's Medium (DMEM) is added to the first container to inhibit an activity of the collagenase and the dispase. In step 908, the umbilical cord is crushed in the first container to release cells into a first solution in the first container. In step 910, the umbilical cord is placed in a second container. In step 912, the umbilical cord is incubated with trypsin. In step 914, fetal bovine serum (FBS) containing Dulbecco's Modified Eagle's Medium (DMEM) is added to the second container to stop activity of trypsin. In step 916, the umbilical cord is crushed in the second container to release cells into a second solution in the second container. In step 918, a mixture of the first solution and the second solution is filtered.

In step 920, a filtrate is centrifuged from to obtain a pellet including mesenchymal stem cells. In step 922, the mesenchymal stem cells are re-suspended in Dulbecco's Modified Eagle's Medium (DMEM) for culturing. In step 924, isolated mesenchymal stem cells are seeded from DMEM. In step 926, the seeded isolated mesenchymal stem cells are incubated until the seeded isolated mesenchymal stem cells reach 70-80% confluence.

Figure 10:
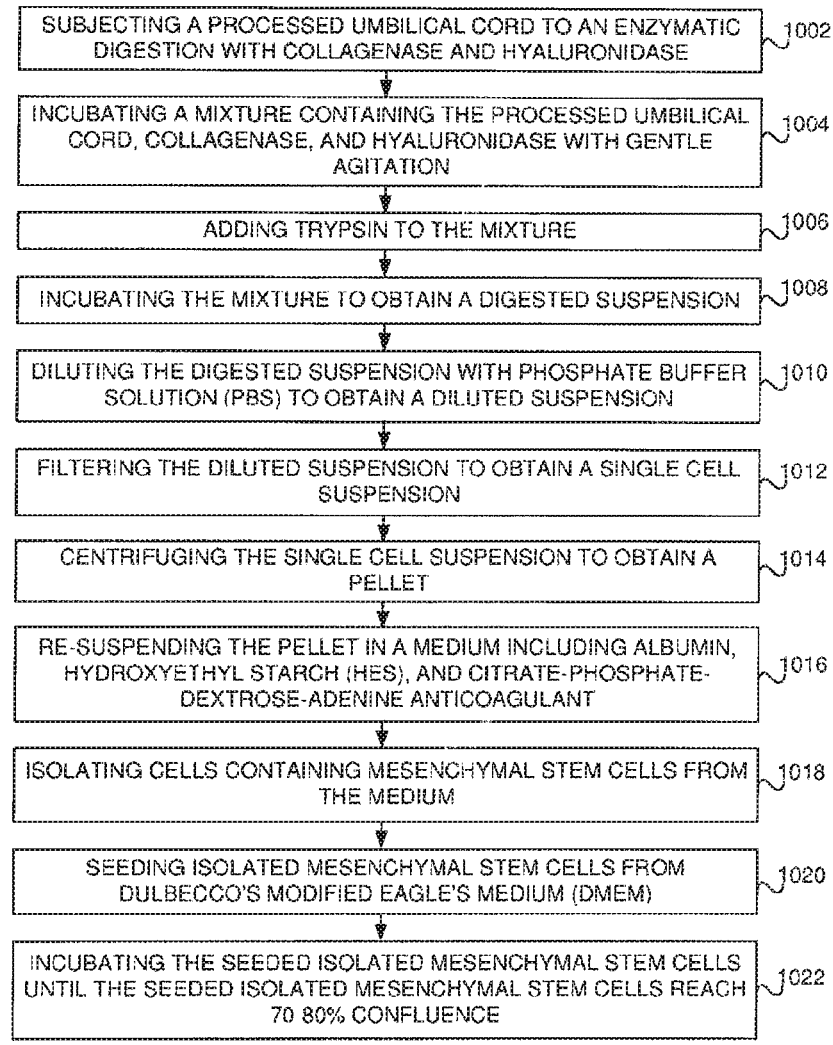
FIG. 10 is a flow diagram illustrating a method for isolating mesenchymal stem cells from an umbilical cord according to an embodiment herein.

FIG. 10 is a flow diagram illustrating a method for isolating mesenchymal stem cells from an umbilical cord according to an embodiment herein. The method includes, in step 1002, a processed umbilical cord is subjected to an enzymatic digestion with collagenase and hyaluronidase. In step 1004, a mixture containing the processed umbilical cord, collagenase, and hyaluronidase are incubated with gentle agitation. In step 1006, trypsin is added to the mixture. In step 1008, the mixture is incubated to obtain a digested suspension. In step 1010, the digested suspension is diluted with phosphate buffer solution (PBS) to obtain a diluted suspension. In step 1012, the diluted suspension is filtered to obtain a single cell suspension.

In step 1014, the single cell suspension is centrifuged to obtain a pellet. In step 1016, the pellet is re-suspended in a medium including albumin, hydroxyethyl starch (HES), and citrate-phosphate-dextrose-adenine anticoagulant. In step 1018, cells containing mesenchymal stem cells are isolated from the medium. In step 1020, isolated mesenchymal stem cells from Dulbecco's Modified Eagle's Medium (DMEM) are seeded. In step 1022, the seeded isolated mesenchymal stem cells are incubated until the seeded isolated mesenchymal stem cells reach 70-80% confluence.

Progenitor cells are early descendants of stem cells that can differentiate to form one or more kinds of cells, but cannot divide and reproduce indefinitely. These cells have a limited proliferative potential, are destined to withdraw from the cell cycle, and give rise to terminally differentiated cells after a finite number of cell divisions. A progenitor cell is often more limited than a stem cell in the kinds of cells it can become. Progenitor cell types have been described as colony-forming cells (CFC) because of their ability to give rise to characteristic cell colonies in a colony formation assay. As part of the proliferative process and in further steps of differentiation, progenitor cells give rise to populations of cells that are known as precursor cells, which are even more restricted in their differentiation capacity. Progenitor cells have potential use in the treatment of various diseases.

Figure 11:
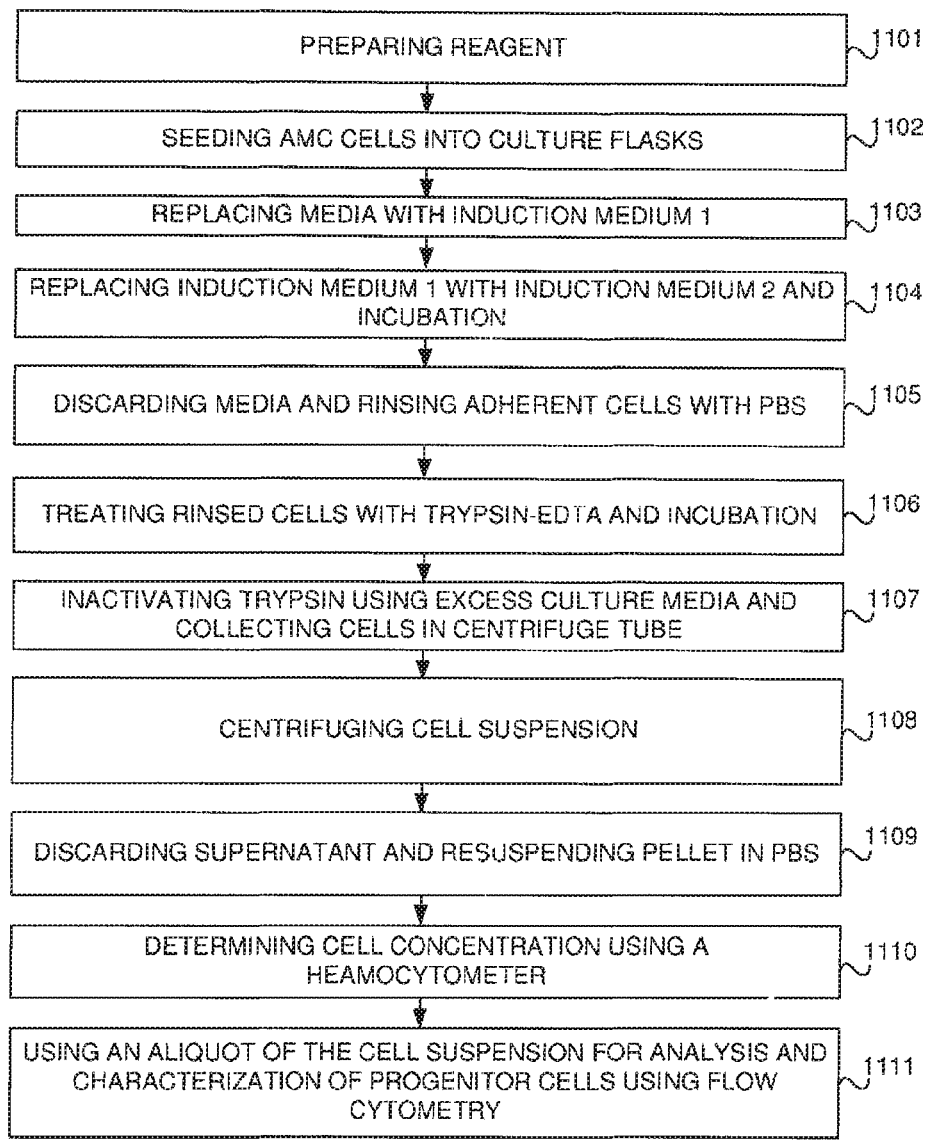
FIG. 11 is a flow diagram illustrating a method of preparing progenitor cells according to an embodiment herein.

FIG. 11 is a flow diagram illustrating a method of preparing progenitor cells according to an embodiment herein. First, the reagent is prepared in step 1101. Here, DMEM medium is added with 10% FBS and 1% antibiotic solution and filter sterilized with a 0.2 µm filter. Two induction mediums are prepared; Induction medium 1 and Induction medium 2. Induction medium 1: DMEM medium is added with 10% FBS, 1% antibiotic solution, and 1 nM 2-Mercaptoethanol filter sterilized with a 0.2 µm filter. Induction medium 2: DMEM medium is added with 1% antibiotic solution, and 1 nM 2-Mercaptoethanol filter sterilized with a 0.2 µm filter.

In step 1102, the AMC cells are seeded into culture flasks at a density of 10,000 cells/cm$^2$. Once the cells reach up to 80% confluency, the media is replaced with induction medium 1 for 24 hours as given in step 1103. After 24 hours, as provided in step 1104, incubation medium 1 is replaced with induction medium 2 and is incubated for 24 hours. In step 1105, after 24 hours, the media is discarded and the adherent cells are rinsed with PBS. The rinsed cells are treated with trypsin-EDTA and incubated at 37° C. for 5 minutes in step 1106. The complete detachment of the adhered cells can be confirmed by viewing the flask under microscope. The trypsin is inactivated using excess culture media and the cells are collected in a centrifuge tube in step 1107. The cell suspension is centrifuged at 300 g for 5 minutes at 20° C. in step 1108, and then the supernatant is discarded and the pellet is resuspended in the PBS in step 1109. The cell concentration is determined using a haemocytometer in step 1110. Thereafter, in step 1111, an aliquot of the cell suspension is used for analysis and characterization of progenitor cells using flow cytometry.

The embodiments herein provide a method for isolation, enrichment, and co-culture of foetal polymix involving two or more components of mesenchymal stem cells derived from but not limited to placenta, amnion, amniotic fluid, chorion and umbilical cord and/or other products of conception (normally discarded after childbirth and hence no ethical issues) including but not limited to hypoxic and/or normoxic/general conditions to give injectable compositions for treatment of a plurality of disorders including, but not limited to, diabetes mellitus, chronic kidney disease, liver cirrhosis, spinal cord injury, cardiac failure, retinitis pigmentosa, autism, muscular dystrophies, non-union fractures, hair loss, knee osteoarthritis, Parkinson's disease, avascular necrosis, Alzheimer's disease, cerebral palsy, multiple sclerosis, anti-aging, and stroke; in animals and/or humans—male and female, congenital to degenerative to developmental to malignant. The foetal polymix obtained has better efficacy and potency as compared to adult stem cells as they are comprised of young stem cells. The foetal polymix is suitably obtained because of a close relationship with embryonic stem cells that have immune privilege characteristics and a broader multipotent plasticity and thereby proliferate faster than adult mesenchymal stem cells and hence are more effective. The method of hypoxic preconditioning of the foetal polymix to enhance bioactive factors improves their survival and potency thereby offering better efficacy in the treatment of disorders.

The embodiments herein provide an injectable composition of foetal polymix is adapted to be administered with or without a combination of various routes of administration not limited to intra-articular, intravenous and intra-thecal injections, intra-muscular injections; local route of administration dither by derma rollers or mesogun, intra-vitreal, periorbital and/or retrobular route and artificial induction of blisters by liquid nitrogen or dermabrasion, for treatment of various disorders. The foetal polymix derived progenitor/precursor target any particular system or disorder.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A method making a foetal polymix composition, said method comprising:
    isolating mesenchymal stem cells (MSCs) from two separate sources, wherein the two sources are amniotic membrane and umbilical cord tissue;
    enriching the MSCs from each source separately; and
    co-culturing the enriched MSCs from each source together in a culture medium under hypoxic conditions, wherein the hypoxic conditions comprise incubation in a carbon dioxide incubator at 37° C. with 1% oxygen concentration, and with a remaining concentration containing carbon dioxide and nitrogen;
    wherein the MSCs from amniotic membrane are isolated and enriched by a process comprising of:
        separating an amniotic membrane from a subjacent chorion;
        transferring fragments of said amniotic membrane to Dulbecco's Modified Eagle's Medium (DMEM) supplemented with fetal bovine serum, glutamine, at least one antibiotic, and non-essential amino acids;
        selecting amniotic membrane fragments from said DMEM;
        fragmenting said selected amniotic membrane fragments into pieces;
        washing said pieces in a phosphate buffer solution;
        subjecting said pieces to a first enzymatic digestion with a trypsin solution to remove epithelial amniotic cells;
        subjecting said pieces to a second enzymatic digestion with another trypsin solution and collagenase;
        subjecting said pieces that are subjected to said first enzymatic digestion and said second enzymatic digestion to fetal bovine serum to obtain a cell suspension;
        filtering said cell suspension;
        centrifuging a filtrate from said cell suspension to obtain a pellet comprising MSCs;
        re-suspending said MSCs in Dulbecco's Modified Eagle's Medium (DMEM) for culturing;
        seeding isolated MSCs with the DMEM into a first culture vessel; and
        maintaining the seeded isolated MSCs until said seeded isolated MSCs reach 70-80% confluence;
    wherein the MSCs from an umbilical cord are isolated and enriched by a process comprising of:
        subjecting a processed umbilical cord to an enzymatic digestion with collagenase and hyaluronidase to form a mixture;
        incubating the mixture containing said processed umbilical cord, collagenase, and hyaluronidase with gentle agitation;
        adding trypsin to the agitated mixture and then incubating to obtain a digested suspension;
        diluting said digested suspension with phosphate buffer solution (PBS) to obtain a diluted suspension;
        filtering said diluted suspension to obtain a single cell suspension;
        centrifuging said single cell suspension to obtain a pellet;
        re-suspending said pellet in a washing solution comprising albumin, hydroxyethyl starch (HES), and citrate-phosphate-dextrose-adenine anticoagulant;
        isolating cells containing MSCs from said washing solution;
        seeding isolated MSCs with DMEM into a second culture vessel; and
        incubating the seeded isolated MSCs until said seeded isolated MSCs reach 70-80% confluence.

2. The method of claim 1, wherein the foetal polymix composition is in a form suitable to treat disorders and diseases comprising diabetes mellitus, cardiomyopathy, chronic kidney disease, critical limb ischemia, liver cirrhosis, spinal cord injury, cardiac failure, cardiomyopathy, retinitis pigmentosa, autism, muscular dystrophies, non-union fractures, hair loss, knee osteoarthritis, Parkinson's disease, avascular necrosis, Alzheimer's disease, cerebral palsy, multiple sclerosis, macular degeneration, anti-aging, stroke, or senescence.

3. The method of claim 1, further comprising wherein the foetal polymix composition is formulated into an injectable composition.

4. The method of claim 1, further comprising wherein the foetal polymix composition is formulated to be suitable for administering via an intravenous route, an intrathecal route, an intra-articular route, an intramuscular route, a derma roller, a mesogun, a local route, a periorbital route, an intravitreal route, or a retrobular route.

5. The method of claim 1, further comprising wherein the foetal polymix composition is formulated to be suitable for treating disorders and diseases.

* * * * *